(12) United States Patent
Sugimoto

(10) Patent No.: US 9,389,178 B2
(45) Date of Patent: Jul. 12, 2016

(54) ANALYSIS DEVICE, ANALYSIS METHOD, OPTICAL ELEMENT AND ELECTRONIC APPARATUS FOR ANALYSIS DEVICE AND ANALYSIS METHOD, AND METHOD OF DESIGNING OPTICAL ELEMENT

(71) Applicant: Seiko Epson Corporation, Tokyo (JP)

(72) Inventor: Mamoru Sugimoto, Chino (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 14/194,903

(22) Filed: Mar. 3, 2014

(65) Prior Publication Data

US 2014/0253920 A1   Sep. 11, 2014

(30) Foreign Application Priority Data

Mar. 5, 2013   (JP) ................................. 2013-042666

(51) Int. Cl.

| | |
|---|---|
| *G01J 4/00* | (2006.01) |
| *G01N 21/552* | (2014.01) |
| *G01N 21/01* | (2006.01) |
| *G01N 21/21* | (2006.01) |
| *G01N 21/65* | (2006.01) |

(52) U.S. Cl.
CPC .............. *G01N 21/553* (2013.01); *G01N 21/01* (2013.01); *G01N 21/21* (2013.01); *G01N 21/554* (2013.01); *G01N 21/65* (2013.01); *G01N 21/658* (2013.01); *Y10T 29/49826* (2015.01)

(58) Field of Classification Search
CPC ........................................................ G01J 4/00
USPC ........................................................ 356/369
See application file for complete search history.

(56) References Cited

U.S. PATENT DOCUMENTS

| | | | |
|---|---|---|---|
| 3,979,184 | A | 9/1976 | Giaever |
| 7,351,588 | B2 | 4/2008 | Poponin |
| 7,399,445 | B2 | 7/2008 | Kuroda et al. |
| 7,639,355 | B2 | 12/2009 | Fattal et al. |
| 7,643,156 | B2 | 1/2010 | Naya et al. |
| 7,705,989 | B2 | 4/2010 | Chaton et al. |

(Continued)

FOREIGN PATENT DOCUMENTS

| | | |
|---|---|---|
| EP | 1857810 A1 | 11/2007 |
| EP | 2372348 A1 | 10/2011 |

(Continued)

OTHER PUBLICATIONS

Cesario, J. et al., "Electromagnetic coupling between a metal nanoparticle grating and a metallic surface", Optics Letters, vol. 3, No. 24, Dec. 15, 2005 (pp. 3404-3406).

(Continued)

*Primary Examiner* — Roy M Punnoose
(74) *Attorney, Agent, or Firm* — Harness, Dickey & Pierce, P.L.C.

(57) ABSTRACT

An analysis device includes an optical element which includes a metal layer, a light transmitting layer on the metal layer, and a plurality of metal particles on the light transmitting layer arranged at a first interval P1 in a first direction and arranged at a second interval P2 in a second direction intersecting the first direction, P1<P2≤Q+P1, a light source which irradiates incident light of linearly polarized light in the first direction onto the optical element, and a detector which detects light emitted from the optical element. Where Q represents the interval between diffraction gratings.

13 Claims, 14 Drawing Sheets

(56) References Cited

U.S. PATENT DOCUMENTS

| | | | |
|---|---|---|---|
| 7,733,491 | B2 | 6/2010 | Kuroda et al. |
| 7,999,934 | B2 | 8/2011 | Naya et al. |
| 8,023,114 | B2 | 9/2011 | Yamamichi et al. |
| 8,314,935 | B2 | 11/2012 | Handa et al. |
| 8,817,263 | B2 | 8/2014 | Sugimoto et al. |
| 8,836,947 | B2 | 9/2014 | Amako et al. |
| 9,057,697 | B2 * | 6/2015 | Amako ............. G01N 21/554 |
| 2003/0059855 | A1 | 3/2003 | Cunningham et al. |
| 2006/0209413 | A1 | 9/2006 | Kim et al. |
| 2009/0002701 | A1 | 1/2009 | Fattal et al. |
| 2010/0220328 | A1 | 9/2010 | Isaka et al. |
| 2010/0233825 | A1 | 9/2010 | Yamada et al. |
| 2011/0114859 | A1 | 5/2011 | Amako et al. |
| 2011/0164252 | A1 | 7/2011 | Handa et al. |
| 2011/0267613 | A1 | 11/2011 | Amako et al. |
| 2011/0273771 | A1 | 11/2011 | Oigawa et al. |
| 2012/0062881 | A1 | 3/2012 | Sakagami et al. |
| 2012/0062882 | A1 | 3/2012 | Sakagami et al. |
| 2012/0062884 | A1 | 3/2012 | Sakagami et al. |
| 2012/0238471 | A1 | 9/2012 | Pinchuk |
| 2012/0274935 | A1 | 11/2012 | Yamada et al. |
| 2012/0276549 | A1 | 11/2012 | Cunningham et al. |
| 2012/0281213 | A1 | 11/2012 | Tyler et al. |
| 2012/0291213 | A1 | 11/2012 | Wu et al. |
| 2012/0309080 | A1 | 12/2012 | Cunningham et al. |
| 2012/0322977 | A1 | 12/2012 | Hill |
| 2012/0327417 | A1 | 12/2012 | Amako et al. |
| 2013/0092823 | A1 | 4/2013 | Amako et al. |
| 2013/0148194 | A1 | 6/2013 | Altug et al. |
| 2013/0176562 | A1 | 7/2013 | Shioi et al. |
| 2013/0182257 | A1 | 7/2013 | Sugimoto et al. |
| 2013/0182258 | A1 | 7/2013 | Amako et al. |
| 2014/0242571 | A1 | 8/2014 | Sugimoto |
| 2014/0242573 | A1 | 8/2014 | Sugimoto |
| 2014/0255913 | A1 * | 9/2014 | Sugimoto ............. G01N 21/65 435/5 |
| 2015/0070693 | A1 | 3/2015 | Sugimoto et al. |
| 2015/0138543 | A1 | 5/2015 | Sugimoto et al. |
| 2015/0233822 | A1 | 8/2015 | Sugimoto et al. |
| 2015/0233835 | A1 | 8/2015 | Sugimoto et al. |

FOREIGN PATENT DOCUMENTS

| | | |
|---|---|---|
| JP | 61-037581 | 8/1986 |
| JP | 2006-003149 A | 1/2006 |
| JP | 2007-024870 A | 2/2007 |
| JP | 2007-064968 A | 3/2007 |
| JP | 2007-508536 A | 4/2007 |
| JP | 2007-538264 A | 12/2007 |
| JP | 2008-014933 A | 1/2008 |
| JP | 2009-085724 A | 4/2009 |
| JP | 2009-115492 A | 5/2009 |
| JP | 2009-115546 A | 5/2009 |
| JP | 2010-531995 A | 9/2010 |
| JP | 2012-132804 A | 7/2012 |
| JP | 2013-148420 A | 8/2013 |
| JP | 2013-148421 A | 8/2013 |
| JP | 2013-221883 A | 10/2013 |
| JP | 2013-231682 A | 11/2013 |
| WO | WO-2005-033335 A2 | 4/2005 |
| WO | WO-2005-114298 A2 | 12/2005 |
| WO | WO-2009-002524 A2 | 12/2008 |
| WO | WO-2012-011998 A2 | 1/2012 |
| WO | WO-2013-157233 A1 | 10/2013 |

OTHER PUBLICATIONS

Chu, Y. et al., "Experimental study of the interaction between localized and propagating surface plasmons", Optics Letters, vol. 34, No. 3, Feb. 1, 2009 (pp. 244-246).

Extended European Search Report for Application No. EP 14 15 7592 dated Oct. 2, 2014 (10 pages).

Y. Chu et al., "Double Resonance Surface Enhanced Raman Scattering Substrates: An Intuitive Coupled Oscillator Model", School of Engineering and Applied Sciences, Harvard University, Optics Express, vol. 19, No. 16, Jul. 19, 2011, pp. 14919-14928.

Chu, Y. et al., "Double-resonance plasmon substrates for surface-enhanced Raman scattering with enhancement at excitation and Stokes frequencies", School of Engineering and Applied Sciences, Harvard University, ACS NANO, vol. 4, No. 5, 2010 (pp. 2804-2810).

Extended European Search Report for Application No. EP 14 15 7811 dated Jul. 14, 2014 (8 pages).

Ordal, M.A. et al., "Optical Properties of the Metals Al, Co, Cu, Au, Fe, Pb, Ni, Pd, Pt, Ag, Ti, and W in the Infrared and Far Infrared", Applied Optics, vol. 22, No. 7, Apr. 1, 1983, pp. 1099-1120.

Extended European Search Report for Application No. EP 15 15 5031 dated Jul. 13, 2015 (9 pages).

* cited by examiner

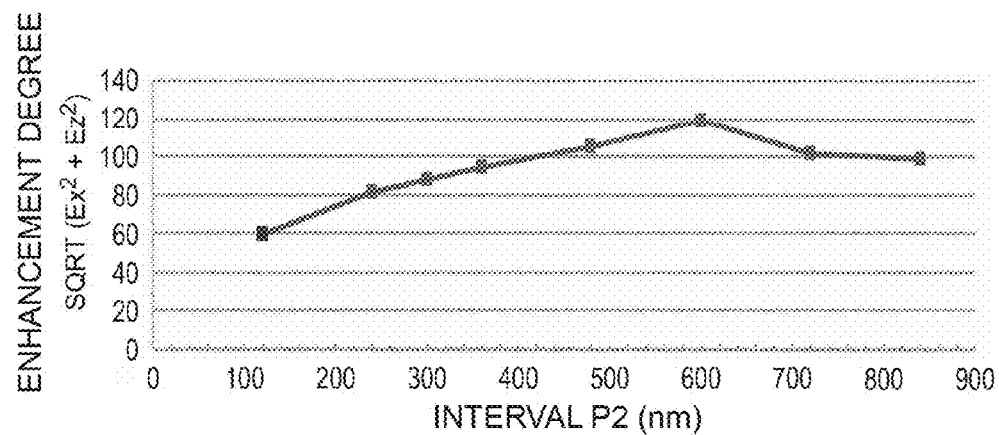
FIG.19
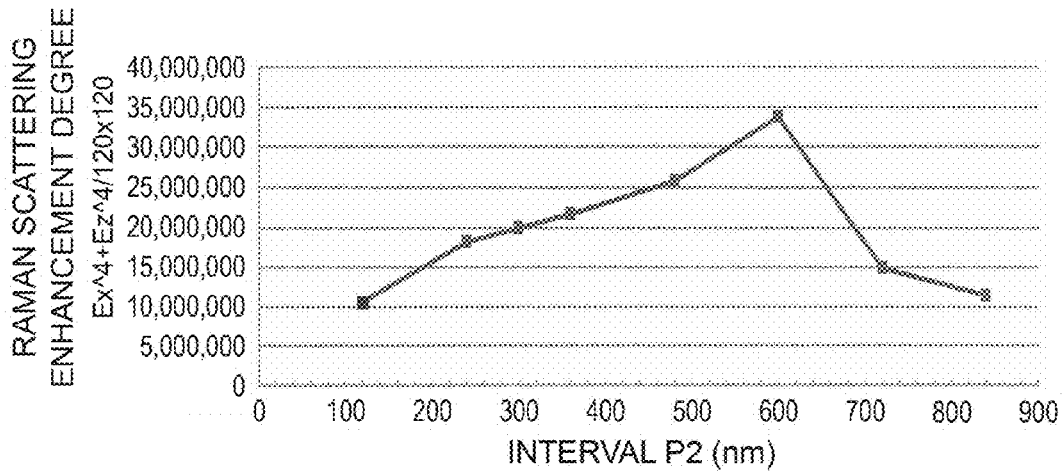
FIG.20
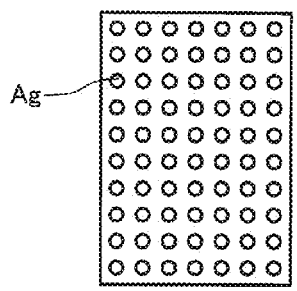 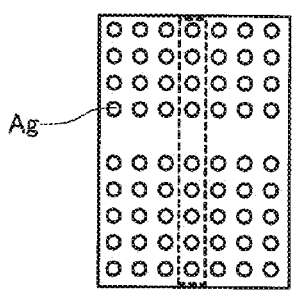
FIG.21A   FIG.21B

ANALYSIS DEVICE, ANALYSIS METHOD, OPTICAL ELEMENT AND ELECTRONIC APPARATUS FOR ANALYSIS DEVICE AND ANALYSIS METHOD, AND METHOD OF DESIGNING OPTICAL ELEMENT

BACKGROUND

1. Technical Field

The present invention relates to an analysis device, an analysis method, an optical element and an electronic apparatus for an analysis device and an analysis method, and a method of designing an optical element.

2. Related Art

In the fields of environment, food, public safety, and the like including the medical and health field, there is a demand for a sensing technique which detects trace substances quickly and simply with high sensitivity and high precision. There are a wide variety of trace substances to be detected, and include, for example, bio-related materials, such as bacteria, viruses, protein, nucleic acids, and various antigens/antibodies, and various compounds including inorganic molecules, organic molecules, and polymers. In the related art, while trace substances are detected by sampling, analysis, and parsing, since a dedicated device is required and an inspection worker needs to be skilled, the analysis in this situation is difficult. For this reason, it takes a lot of time (several days or more) for an inspection result to be obtained. Thus, there is a great need for quick and simple detection, and therefore, it is desirable to develop a sensor which can meet this need.

For example, from expectations of comparative ease of integration and less influence by an inspection and measurement environment, there is a growing interest in a sensor which uses surface plasmon resonance (SPR), or a sensor which uses surface-enhanced Raman scattering (SERS).

For the purpose of sensing with higher sensitivity, as an example of a sensor element having a structure which realizes a hybrid mode, in which both modes of a localized surface plasmon (LSP) and a propagated surface plasmon (PSP) are resonated simultaneously, OPTICS LETTERS, Vol. 34, No. 3, 2009, 244-246 suggests a sensor element, called GSPP (Gap type Surface Plasmon Polariton). OPTICS LETTERS, Vol. 30, No. 24, 2005, 3404-3406 describes the fundamental matters of electromagnetic coupling of LSP and PSP, and discloses an element having a configuration in which LSP and PSP interfere with each other constructively (International Publication No. 2009/002524 and International Publication No. 2005/114298).

The sensor disclosed in International Publication No. 2009/002524 has a layer in which nanoparticles formed on a substrate made of a dielectric are arranged regularly in a lattice shape. The particle layer is an array in which a particle size is 2 nm to 200 nm, if the particles are arranged in a square lattice shape, the particles are arranged at an interval between particles of 50 nm to several µm, and if the particles are arranged so as to form a diffraction grating, the particles are arranged in a row at an interval of 1 nm to 10 nm and at an interval between rows of equal to or greater than 0.1 µm.

The sensor disclosed in International Publication No. 2005/114298 has a vapor deposition layer which is called a resonance mirror on a substrate and is made of silver, gold, or aluminum to have a thickness of 200 nm to 500 nm. Then, the sensor has a dielectric layer which is called a light transmitting layer formed on the vapor deposition layer to have a thickness of smaller than 50 nm, and a particle layer which is called a nanoparticle layer formed on the dielectric layer and has particles of gold, silver, or the like arranged therein. The particle layer is an array in which the particle size is 50 nm to 200 nm, and the particles are arranged regularly at even intervals between particles from an interval smaller than the wavelength of incident light to an interval obtained by adding 0 nm to 20 nm to the particle size.

However, in the sensors disclosed in International Publication No. 2009/002524 and International Publication No. 2005/114298, the relationship between the wavelength or polarization sate of incident light and the arrangement of the array is not taken into consideration, and for this reason, a sufficient signal amplification degree is not necessarily obtained.

Although OPTICS LETTERS, Vol. 34, No. 3, 2009, 244-246 and OPTICS LETTERS, Vol. 30, No. 24, 2005, 3404-3406 suggest a system which uses the interaction between the localized surface plasmon and the propagated surface plasmon, there is a problem in that Hot Spot Density (HSD) is low.

SUMMARY

An advantage of some aspects of the invention is that it provides an optical element with a large enhancement degree of light based on plasmon to be excited by light irradiation and high HSD, and a method of designing an optical element. Another advantage of some aspects of the invention is that it provides an analysis device and an electronic apparatus including the optical element, and an analysis method.

An aspect of the invention is directed to an analysis device including an optical element which includes a metal layer, a light transmitting layer provided on the metal layer to transmit light, and a plurality of metal particles arranged at a first interval in a first direction and arranged at a second interval in a second direction intersecting the first direction on the light transmitting layer, a light source which irradiates incident light of linearly polarized light in the same direction as the first direction onto the optical element, and a detector which detects light emitted from the optical element, in which the arrangement of the metal particles of the optical element satisfies the relationship of Expression (1).

$$P1 < P2 \leq Q + P1 \tag{1}$$

Here, P1 represents the first interval, P2 represents the second interval, and Q represents the interval between diffraction gratings given by Expression (2) when an angular frequency of a localized surface plasmon excited in the metal particle column is $\omega$, a dielectric constant of a metal constituting the metal layer is $\in(\omega)$, a dielectric constant around the metal layer is $\in$, light speed in a vacuum is $c$, and an irradiation angle of incident light which is an inclination angle of incident light from a thickness direction of the light transmitting layer is $\theta$.

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
$$(m = \pm 1, \pm 2, \ldots) \tag{2}$$

According to this analysis device, an optical element with a large enhancement degree of light based on plasmon and high HSD is provided, whereby it is possible to easily perform detection and measurement of trace substances.

In the analysis device according to the aspect of the invention, the interval P2 may satisfy the relationship of 60 nm ≤ P2 ≤ 1310 nm.

According to the analysis device of this configuration, since an optical element with a larger enhancement degree of light based on plasmon is provided, it is possible to more easily perform detection and measurement of trace substances.

In the analysis device according to the aspect of the invention, the interval P2 may satisfy the relationship of 60 nm≤P2≤660 nm.

According to the analysis device of this configuration, since an optical element with a larger enhancement degree of light based on plasmon is provided, it is possible to more easily perform detection and measurement of trace substances.

In the analysis device according to the aspect of the invention, the interval P1 may satisfy the relationship of 60 nm≤P1≤120 nm.

According to the analysis device of this configuration, since an optical element with a larger enhancement degree of light based on plasmon is provided, it is possible to more easily perform detection and measurement of trace substances.

In the analysis device according to the aspect of the invention, the size D of the metal particles in the first direction may satisfy the relationship of 30 nm≤D≤72 nm.

According to the analysis device of this configuration, since an optical element with a larger enhancement degree of light based on plasmon is provided, it is possible to more easily perform detection and measurement of trace substances.

In the analysis device according to the aspect of the invention, the size T of the metal particles in a height direction may satisfy the relationship of 4 nm≤T≤20 nm.

According to the analysis device of this configuration, since an optical element with a larger enhancement degree of light based on plasmon is provided, it is possible to more easily perform detection and measurement of trace substances.

In the analysis device according to the aspect of the invention, the light transmitting layer may be a dielectric layer in which a height direction of the metal particles is a thickness direction, and the thickness G of the dielectric layer may satisfy the relationship of 20 nm≤G≤60 nm.

According to the analysis device of this configuration, since an optical element with a larger enhancement degree of light based on plasmon is provided, it is possible to more easily perform detection and measurement of trace substances.

In the analysis device according to the aspect of the invention, the detector may detect Raman scattering light enhanced by the optical element.

According to the analysis device of this configuration, since an optical element with a larger enhancement degree of light based on plasmon is provided, it is possible to enhance Raman scattering light and to easily perform measurement of trace substances.

In the analysis device according to the aspect of the invention, the light source may irradiate incident light having a wavelength greater than the size T in the height direction and the size D in the first direction of the metal particles onto the optical element.

According to the analysis device of this configuration, since it is possible to further extract the capability of an optical element with a large enhancement degree of light based on plasmon, it is possible to easily perform detection, measurement, and the like of trace substances.

Another aspect of the invention is directed to an optical element which is provided in the analysis device according to the aspect of the invention and onto which linearly polarized light in the same direction as the first direction is irradiated.

This optical element has a large enhancement degree of light based on plasmon.

Still another aspect of the invention is directed to an analysis method which irradiates incident light onto an optical element and detects light emitted from the optical element with the irradiation of incident light to analyze an object stuck to the surface of the optical element, in which the optical element includes a metal layer, a light transmitting layer provided on the metal layer to transmit light, and a plurality of metal particles arranged at a first interval in a first direction and arranged at a second interval in a second direction intersecting the first direction on the light transmitting layer, the metal particles of the optical element are arranged so as to satisfy the relationship of Expression (1), and incident light of linearly polarized light in the same direction as the first direction is irradiated onto the optical element.

$$P1 < P2 \leq Q + P1 \quad (1)$$

Here, P1 represents the first interval, P2 represents the second interval, and Q represents the interval between diffraction gratings given by Expression (2) when an angular frequency of a localized surface plasmon excited in the metal particle column is ω, a dielectric constant of a metal constituting the metal layer is $\in(\omega)$, a dielectric constant around the metal layer is $\in$, light speed in a vacuum is c, and an irradiation angle of incident light which is an inclination angle of incident light from a thickness direction of the light transmitting layer is θ.

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
$$(m = \pm 1, \pm 2, \ldots) \quad (2)$$

According to this analysis method, since an optical element with a large enhancement degree based on plasmon and high HSD is used, it is possible to easily detect and measure trace substances.

Yet another aspect of the invention is directed to a method of designing an optical element, in which the optical element includes a metal layer, a light transmitting layer provided on the metal layer to transmit light, and a plurality of metal particles arranged at a first interval in a first direction and arranged at a second interval in a second direction intersecting the first direction on the light transmitting layer, and the metal particles are arranged so as to satisfy the relationship of Expression (1).

$$P1 < P2 \leq Q + P1 \quad (1)$$

Here, P1 represents the first interval, P2 represents the second interval, and Q represents the interval between diffraction gratings given by Expression (2) when an angular frequency of a localized surface plasmon excited in the metal particle column is ω, a dielectric constant of a metal constituting the metal layer is $\in(\omega)$, a dielectric constant around the metal layer is $\in$, light speed in a vacuum is c, and an irradiation angle of incident light which is an inclination angle of incident light from a thickness direction of the light transmitting layer is θ.

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
$$(m = \pm 1, \pm 2, \ldots) \quad (2)$$

According to this design method, it is possible to design an optical element with a large enhancement degree of light based on plasmon and high HSD.

Still yet another aspect of the invention is directed to a method of designing an optical element, in which the optical element includes a metal layer, a light transmitting layer provided on the metal layer to transmit light, and a plurality of metal particles arranged at a first interval in a first direction and arranged at a second interval in a second direction intersecting the first direction on the light transmitting layer, and the metal particles are arranged in a matrix in the first direction and the second direction such that a localized surface plasmon and a propagated surface plasmon occur.

According to this design method, it is possible to design an optical element with a large enhancement degree of light based on plasmon.

Further, another aspect of the invention is directed to an electronic apparatus including the analysis device according to the aspect of the invention, a calculation unit which calculates diagnostic information such as health and medical information on the basis of detection information from the detector, a storage unit which stores the health and medical information, and a display unit which displays the health and medical information.

According to this electronic apparatus, the electronic apparatus includes an optical element with a large enhancement degree of light based on plasmon, whereby it is possible to easily detect trace substances and provide high-precision health and medical information.

In the electronic apparatus according to the aspect of the invention, the health and medical information may include information relating to the presence/absence or the amount of at least one bio-related material selected from a group consisting of bacteria, viruses, protein, nucleic acids, and antigens/antibodies, or at least one compound selected from inorganic molecules and organic molecules.

According to the electronic apparatus of this configuration, it is possible to provide useful health and medical information.

BRIEF DESCRIPTION OF THE DRAWINGS

Embodiments of the invention will be described with reference to the accompanying drawings, wherein like numbers reference like elements.

FIG. 19 is a graph showing the relationship between an enhancement degree and an interval according to an experimental example.

FIG. 20 is a graph showing the relationship between a Raman scattering enhancement degree and an interval according to an experimental example.

FIGS. 21A and 21B are schematic views showing an example of a model according to an experimental example.

DESCRIPTION OF EXEMPLARY EMBODIMENTS

Hereinafter, some embodiments of the invention will be described. In the following embodiments, an example of the invention will be described. It should be noted that the invention is not limited to the following embodiments, and various modifications may be carried out within a scope not departing from the gist of the invention. Not all configurations described below are essential to the invention.

1. Optical Element

Figure 1:
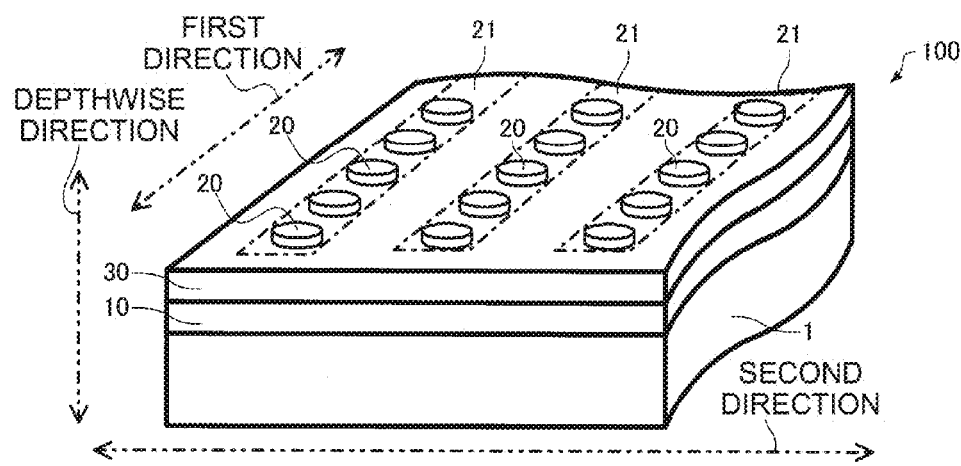
FIG. 1 is a perspective view schematically showing an optical element of an embodiment.
Figure 2:
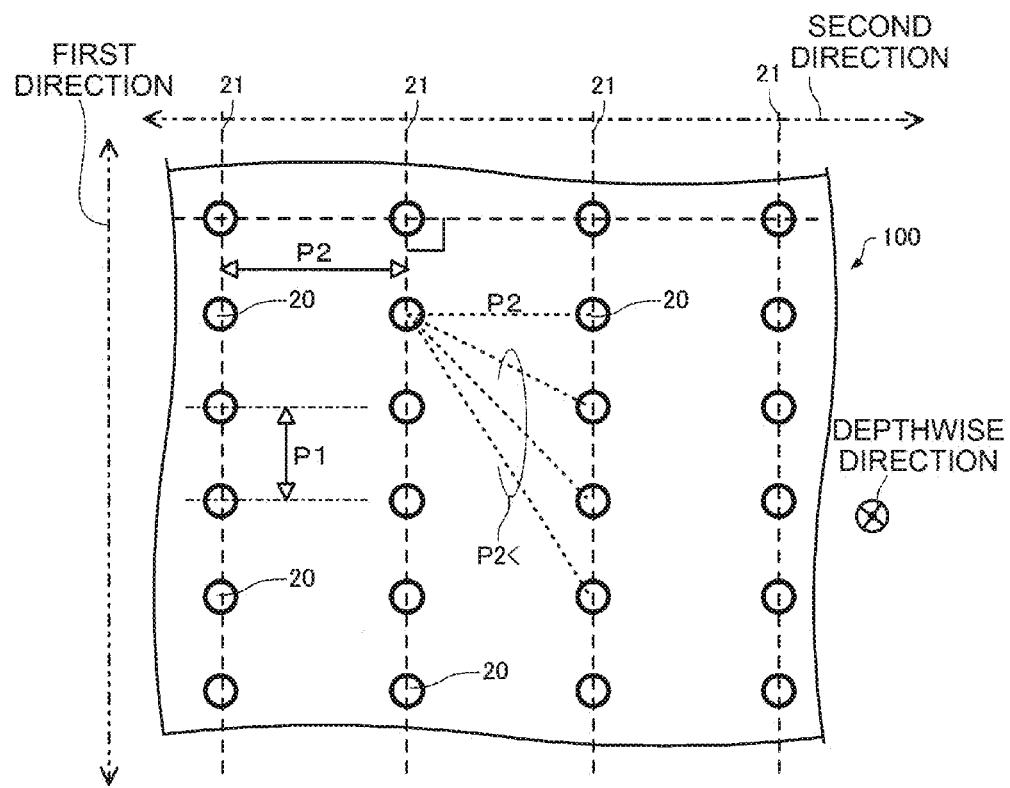
FIG. 2 is a schematic view when the optical element of the embodiment is viewed from a thickness direction of a light transmitting layer.
Figure 3:
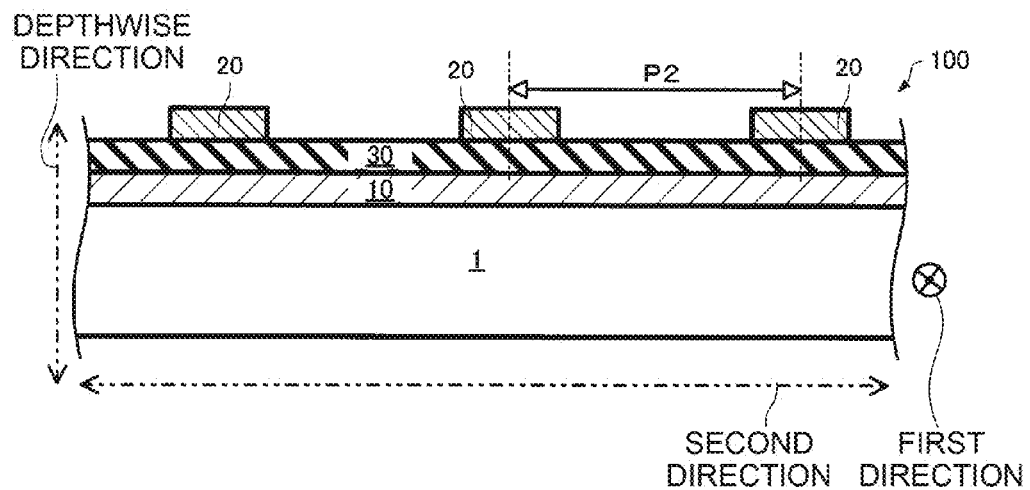
FIG. 3 is a schematic view of a cross-section perpendicular to a first direction of the optical element of the embodiment.
Figure 4:
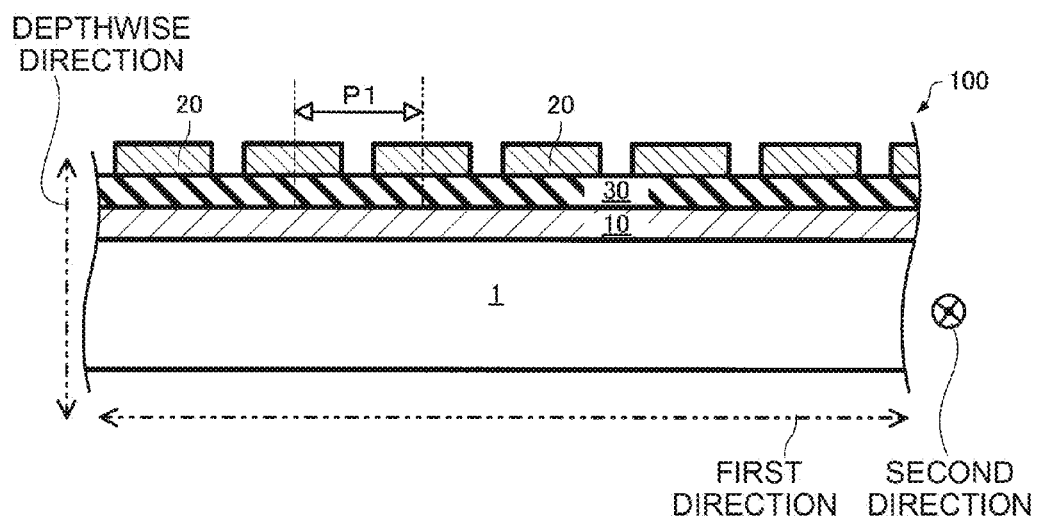
FIG. 4 is a schematic view of a cross-section perpendicular to a second direction of the optical element of the embodiment.
Figure 5:
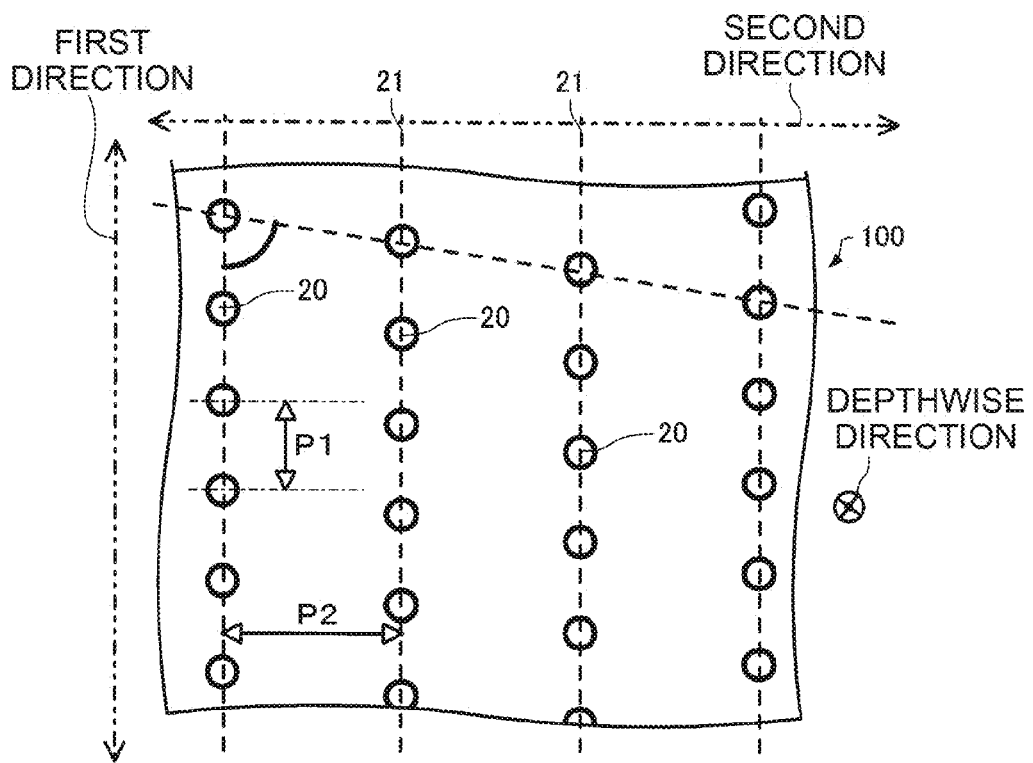
FIG. 5 is a schematic view when the optical element of the embodiment is viewed from the thickness direction of the light transmitting layer.

FIG. 1 is a schematic view of a cross-section of an optical element 100 of this embodiment. FIG. 2 is a schematic view when the optical element 100 of this embodiment is viewed in plan view (viewed from a thickness direction of a light transmitting layer). FIGS. 3 and 4 are schematic views of a cross-section of the optical element 100 of this embodiment. FIG. 5 is a schematic view when the optical element 100 of this embodiment is viewed from the thickness direction of the light transmitting layer. The optical element 100 of this embodiment includes a metal layer 10, metal particles 20, and a light transmitting layer 30.

1.1. Metal Layer

The metal layer 10 is not particularly limited insofar as a metal surface which does not transmit light is provided, and for example, may have a thick plate shape or a shape of a film, a layer, or a membrane. For example, the metal layer 10 may be provided on a substrate 1. In this case, the substrate 1 is not particularly limited, and it is preferable that the substrate 1 is less likely to affect a propagated surface plasmon excited in the metal layer 10. As the substrate 1, for example, a glass substrate, a silicon substrate, a resin substrate, or the like may be used. The shape of the surface of the substrate 1 on which the metal layer 10 is provided is not particularly limited. If a regular structure is formed on the surface of the metal layer 10, the substrate may have a surface corresponding to the regular structure, and if the surface of the metal layer 10 is a plane, the surface of the substrate may be a plane. In the example of FIGS. 1 to 5, the metal layer 10 is provided on the surface (plane) of the substrate 1.

Here, although the expression of "plane" is used, the related expression does not indicate a mathematically strict plane which is flat (smooth) with no slight unevenness. For example, the surface has unevenness due to constituent atoms or unevenness due to a secondary structure (crystal, grain aggregate, grain boundary, or the like) of a constituent material, and is not a strict plane from a microscopic viewpoint. However, even in this case, from a more macroscopic viewpoint, unevenness is less noticeable, and the surface is observed to such an extent that the surface may be referred to as a plane. Accordingly, in this specification, it is assumed that, when the surface is recognizable as a plane from a more macroscopic viewpoint, the surface is referred to as a plane.

In this embodiment, the thickness direction of the metal layer 10 coincides with the thickness direction of the light transmitting layer 30 described below. In this specification, the thickness direction of the metal layer 10 or the thickness direction of the light transmitting layer 30 may be referred to as a depthwise direction, a height direction, or the like upon description of the metal particles 20 described below. For example, if the metal layer 10 is provided on the surface of the substrate 1, the normal direction of the surface of the substrate 1 may be referred to as a thickness direction, a depthwise direction, or a height direction.

For example, the metal layer 10 can be formed using a method, such as vapor deposition, sputtering, casting, machining, or the like. If the metal layer 10 is provided on the substrate 1, the metal layer 10 may be provided on the entire surface of the substrate 1 or may be provided on a part of the surface of the substrate 1. The thickness of the metal layer 10 is not particularly limited insofar as the propagated surface plasmon is excited in the metal layer 10, and for example, can be equal to or greater than 10 nm and equal to or smaller than 1 mm, preferably, equal to or greater than 20 nm and equal to or smaller than 100 µm, and more preferably, equal to or greater than 30 nm and equal to or smaller than 1 µm.

The metal layer 10 is made of a metal in which there are an electric field given by incident light and an electric field such that a polarization induced by the electric field vibrates in an inverse phase, that is, a metal which can have a dielectric constant such that, if a specific electric field is given, a real part of a dielectric function has a negative value (has a negative dielectric constant), and a dielectric constant of an imaginary part is smaller than the absolute value of the dielectric constant of the real part. Examples of a metal which can have a dielectric constant in a visible light region include gold, silver, aluminum, copper, platinum, an alloy thereof, and the like. The surface of (the end surface in the thickness direction) the metal layer 10 may or may not have a specific crystal plane.

The metal layer 10 has a function of causing a propagated surface plasmon to be generated in the optical element 100 of this embodiment. Light is incident on the metal layer 10 under the following conditions, whereby the propagated surface plasmon is generated near the surface (the end surface in the thickness direction) of the metal layer 10. In this specification, a quantum of vibration in which vibration of electric charges near the surface of the metal layer 10 and electromagnetic waves are coupled is called surface plasmon plariton (SPP). The propagated surface plasmon generated in the metal layer 10 can interact (hybrid) with a localized surface plasmon generated in the metal particles 20 described below under certain conditions.

1.2. Metal Particle

The metal particles 20 are provide to be separated from the metal layer 10 in the thickness direction. The metal particles 20 may be arranged to be spatially separated from the metal layer 10, and other substances, such as an insulator, a dielectric, and a semiconductor, may be provided between the metal particles 20 and the metal layer 10 in a single layer or a plurality of layers. In the example of FIGS. 1 to 5 of this embodiment, the light transmitting layer 30 is provided on the metal layer 10, and the metal particles 20 are formed on the light transmitting layer 30, whereby the metal layer 10 and the metal particles 20 are arranged to be separated in the thickness direction of the light transmitting layer.

The shape of the metal particles 20 is not particularly limited. For example, the shape of the metal particles 20 may be a circular shape, an elliptical shape, a polygonal shape, an undefined shape, or a combined shape thereof when projected in the thickness direction of the metal layer 10 or the light transmitting layer 30 (in plan view from the thickness direction), or may be a circular shape, an elliptical shape, a polygonal shape, an undefined shape, or a combined shape thereof when projected in a direction orthogonal to the thickness direction. In the example of FIGS. 1 to 5, although all the metal particles 20 are drawn in a columnar shape having a center axis in the thickness direction of the light transmitting layer 30, the shape of the metal particles 20 is not limited thereto.

The size T in the height direction of the metal particles 20 indicates the length of a zone when the metal particles 20 can be cut by a plane perpendicular to the height direction, and is equal to or greater than 1 nm and equal to or smaller than 100 nm. The size in a first direction orthogonal to the height direction of the metal particles 20 indicates the length of a zone when the metal particles 20 can be cut by a plane perpendicular to the first direction, and is equal to or greater than 5 nm and equal to or smaller than 200 nm. For example, if the shape of the metal particles 20 is a columnar shape with the height direction as a center axis, the size (the height of the column) in the height direction of the metal particles 20 is equal to or greater than 1 nm and equal to or smaller than 100 nm, preferably, equal to or greater than 2 nm and equal to or smaller than 50 nm, more preferably, equal to or greater than 3 nm and equal to or smaller than 30 nm, and still more preferably, equal to or greater than 4 nm and equal to or smaller than 20 nm. If the shape of the metal particles 20 is a columnar shape with the height direction as a center axis, the size (the diameter of the bottom surface of the column) in the first direction of the metal particles 20 is equal to or greater than 10 nm and equal to or smaller than 200 nm, preferably, equal to or greater than 20 nm and equal to or smaller than 150 nm, more preferably, equal to or greater than 25 nm and equal to or smaller than 100 nm, and still more preferably, equal to or greater than 30 nm and equal to or smaller than 72 nm.

Although the shape and material of the metal particles 20 are arbitrary insofar as a localized surface plasmon is generated by irradiation of incident light, examples of a material in which a localized surface plasmon can be generated by light near visible light include gold, silver, aluminum, copper, platinum, an alloy thereof, and the like.

The metal particles 20 can be formed by, for example, a method which performs patterning after a thin film is formed by sputtering, vapor deposition, or the like, a microcontact print method, a nanoimprint method, or the like. The metal particles 20 may be formed by a colloid chemical method, and may be arranged at a position to be separated from the metal layer 10 by an appropriate method.

The metal particles 20 have a function of causing a localized surface plasmon to be generated in the optical element 100 of this embodiment. Incident light is irradiated onto the metal particles 20 under the following conditions, whereby the localized surface plasmon can be generated around the metal particles 20. The localized surface plasmon generated in the metal particles 20 can interact (hybrid) with the propagated surface plasmon generated in the metal layer 10 under certain conditions.

1.3. Arrangement of Metal Particles

As shown in FIGS. 1 to 5, a plurality of metal particles 20 are arranged to constitute metal particle columns 21. The metal particles 20 are arranged in the first direction orthogonal to the thickness direction of the metal layer 10 in the metal particle columns 21. In other words, the metal particle columns 21 have a structure in which a plurality of metal particles 20 are arranged in the first direction orthogonal to the height direction. If the metal particles 20 have a longitudinal shape (an anisotropic shape), the first direction in which the metal particles 20 are arranged may not coincide with the longitudinal direction. The number of metal particles 20 which are arranged in one metal particle column 21 may be plural, and preferably, is equal to or greater than 10.

The interval of the metal particles 20 in the first direction in the metal particle columns 21 is defined as an interval P1 (see FIGS. 2 to 5). The interval P1 indicates the inter-center distance (pitch) of two metal particles 20 in the first direction. If the metal particles 20 have a columnar shape with the thickness direction of the metal layer 10 as a center axis, the inter-particle distance of two metal particles 20 in the metal particle columns 21 is equal to a length obtained by subtracting the diameter of the column from the interval P1. If the inter-particle distance is small, there is a tendency that the effect of the localized surface plasmon acting between the particles increases, and an enhancement degree increases. The inter-particle distance may be equal to or greater than 5 nm and equal to or smaller than 1 μm, preferably, equal to or greater than 5 nm and equal to or smaller than 100 nm, and more preferably, equal to or greater than 5 nm and equal to or smaller than 30 nm.

The interval P1 of the metal particles 20 in the first direction in the metal particle columns 21 is equal to or greater than 10 nm and equal to or smaller than 1 μm, preferably, equal to or greater than 20 nm and equal to or smaller than 800 nm, more preferably, equal to or greater than 30 nm and equal to or smaller than 780 nm, and still more preferably, equal to or greater than 50 nm and equal to or smaller than 700 nm.

Although the metal particle columns 21 are constituted by a plurality of metal particles 20 arranged at the interval P1 in the first direction, the distribution, intensity, and the like of the localized surface plasmon generated in the metal particles 20 also depend on the arrangement of the metal particles 20. Accordingly, the localized surface plasmon which interacts with the propagated surface plasmon generated in the metal layer 10 is a localized surface plasmon taking into consideration the arrangement of the metal particles 20 in the metal particle columns 21, as well as a localized surface plasmon generated in the single metal particle 20.

As shown in FIGS. 1 to 5, the metal particle columns 21 are arranged at an interval P2 in a second direction intersecting the thickness direction of the metal layer 10 and the first direction. The number of metal particle columns 21 arranged may be plural, and preferably, is equal to or greater than 10.

Here, the interval of adjacent metal particle columns 21 in the second direction is defined as the interval P2. The interval P2 indicates the inter-center distance (pitch) of two metal particle columns 21 in the second direction. If the metal particle columns 21 are constituted by a plurality of columns 22, the interval P2 indicates the distance between the position of a center of a plurality of columns 22 in the second direction and the position of a center of a plurality of columns 22 of an adjacent metal particle column 21 in the second direction (see FIG. 9).

The interval P2 between the metal particle columns 21 is set under conditions described in "1.3.1. Propagated Surface Plasmon and Localized Surface Plasmon", and for example, may be equal to or greater than 10 nm and equal to or smaller than 10 μm, preferably, equal to or greater than 20 nm and equal to or smaller than 2 μm, more preferably, equal to or greater than 30 nm and equal to or smaller than 1500 nm, still more preferably, equal to or greater than 60 nm and equal to or smaller than 1310 nm, and particularly preferably, equal to or greater than 60 nm and equal to or smaller than 660 nm.

The angle between a line in the first direction in which the metal particle columns 21 extend and a line which connects two closest metal particles 20 respectively belonging to adjacent metal particle columns 21 is not particularly limited, and may be a right angle. For example, as shown in FIG. 2, the angle between both lines may be a right angle, or as shown in FIG. 5, the angle between both lines may not be a right angle. That is, if the arrangement of the metal particles 20 when viewed from the thickness direction is regarded as a two-dimensional lattice with the positions of the metal particles 20 as lattice points, an irreducible fundamental unit lattice may have a rectangular shape or a parallelogram shape. If the angle between the line in the first direction in which the metal particle columns 21 extend and the line which connects two closest metal particles 20 respectively belonging to adjacent metal particle columns 21 is not a right angle, the interval between two closest metal particles 20 respectively belonging to adjacent metal particle columns 21 may be defined as the interval P2.

1.3.1. Propagated Surface Plasmon and Localized Surface Plasmon

Figure 6:
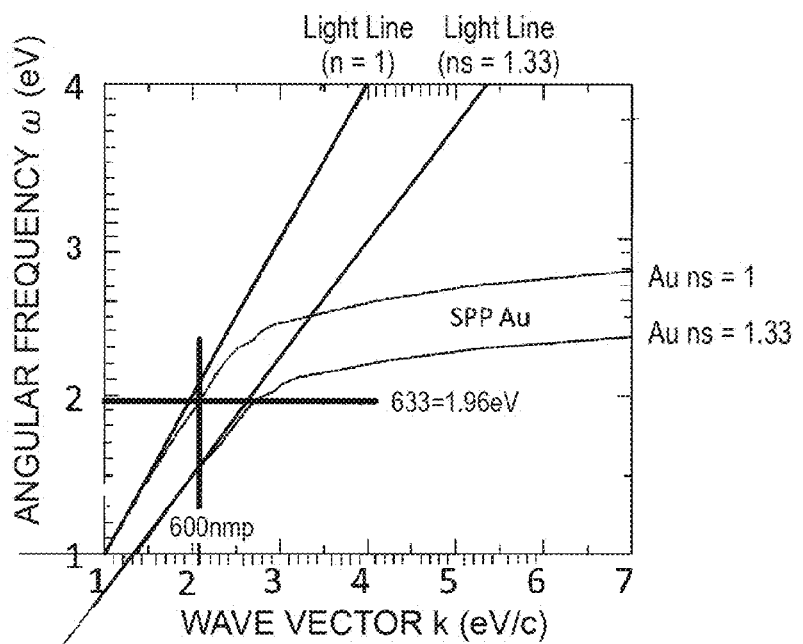
FIG. 6 is a graph of a dispersion relation representing dispersion curves of incident light and gold.

First, the propagated surface plasmon will be described. FIG. 6 is a graph of a dispersion relation representing dispersion curves of incident light and gold. Usually, even if light is irradiated onto the metal layer 10 at an incidence angle (irradiation angle θ) of 0 to 90 degrees, the propagated surface plasmon is not generated. For example, this is because, if the metal layer 10 is made of Au, as shown in FIG. 6, a light line and a dispersion curve of SPP of Au have no intersection point. Even if the refractive index of a medium through which light passes changes, since SPP of Au changes depending on an ambient refractive index, there is no intersection point. In order to cause the propagated surface plasmon with an intersection point to be generated, there is a method in which a metal layer is provided on a prism like the Kretschmann arrangement, and the wavenumber of incident light increases with the refractive index of the prism, or a method in which the wavenumber of a light line increases with a diffraction grating. FIG. 6 is a graph showing a so-called dispersion relation (the vertical axis is an angular frequency [ω (eV)], and the horizontal axis is a wave vector [k (eV/c)]).

The angular frequency ω (eV) on the vertical axis of the graph of FIG. 6 has a relationship of λ (nm)=1240/ω (eV), and can be converted to wavelength. The wave vector k (eV/c) on the horizontal axis of the graph has a relationship of k (eV/c)=2π·2/[λ (nm)/100]. Accordingly, for example, if λ=600 nm, k=2.09 (eV/c). The irradiation angle is the irradiation angle of incident light, and is the inclination angle from the thickness direction of the metal layer 10 or the light transmitting layer 30 or from the height direction of the metal particles 20.

Although FIG. 6 shows the dispersion curve of SPP of Au, in general, when the angular frequency of incident light incident on the metal layer 10 is ω, light speed in a vacuum is c, the dielectric constant of a metal constituting the metal layer 10 is $\in(\omega)$, and an ambient dielectric constant is $\in$, the dispersion curve of SPP of the metal is given by Expression (3).

$$K_{SPP}=\omega/c[\in\cdot\in(\omega)/(\in+\in(\omega)]^{1/2} \quad (3)$$

When the irradiation angle of incident light, that is, the inclination angle from the thickness direction of the metal layer 10 or the light transmitting layer 30 or from the height direction of the metal particles 20 is θ, the wavenumber K of incident light which passes through virtual diffraction gratings having an interval Q can be expressed by Expression (4).

$$K=n\cdot(\omega/c)\cdot\sin\theta+m\cdot2\pi/Q(m=\pm1,\pm2,\ldots) \quad (4)$$

This relationship appears as a line, instead of a curve, on the graph of the dispersion relation.

Note that n is an ambient refractive index, when an extinction coefficient is κ, a real part $\in'$ and an imaginary part $\in''$ of a relative dielectric constant $\in$ at a frequency of light are respectively given by $\in'=n^2-\kappa^2$ and $\in''=2n\kappa$, and if an ambient medium is transparent, since $\kappa\sim0$, $\in$ is a real number, becomes $\in=n^2$, and is given by $n=\in^{1/2}$.

In the graph of the dispersion relation, if the dispersion curve (Expression (3)) of SPP of the metal and the line (Expression (4)) of diffracted light have an intersection point, the propagated surface plasmon is excited. That is, if the relationship of $K_{SPP}=K$, the propagated surface plasmon is excited in the metal layer 10.

Accordingly, Expression (2) is obtained from Expression (3) and Expression (4).

$$(\omega/c)\cdot\{\in\cdot\in(\omega)/(\in+\in(\omega))\}^{1/2}=\in^{1/2}\cdot(\omega/c)\cdot\sin\theta+2m\pi/Q$$
$$(m=\pm1,\pm2,\ldots) \quad (2)$$

It is understood that, if the relationship of Expression (2) is satisfied, the propagated surface plasmon is excited in the metal layer 10. In this case, in the example of SPP of Au of FIG. 6, change in θ and m can cause change in the slope and/or slice of the light line, and it is possible to cause the line of the light line to intersect the dispersion curve of SPP of Au.

Next, the localized surface plasmon will be described.

The condition for causing the localized surface plasmon to be generated in the metal particles 20 is given by the following expression using a real part of a dielectric constant.

$$\text{Real}[\in(\omega)]=-2\in \quad (5)$$

If the ambient refractive index n is 1, since $\in=n^2-\kappa^2=1$, Real $[\in(\omega)]=-2$.

Figure 7:
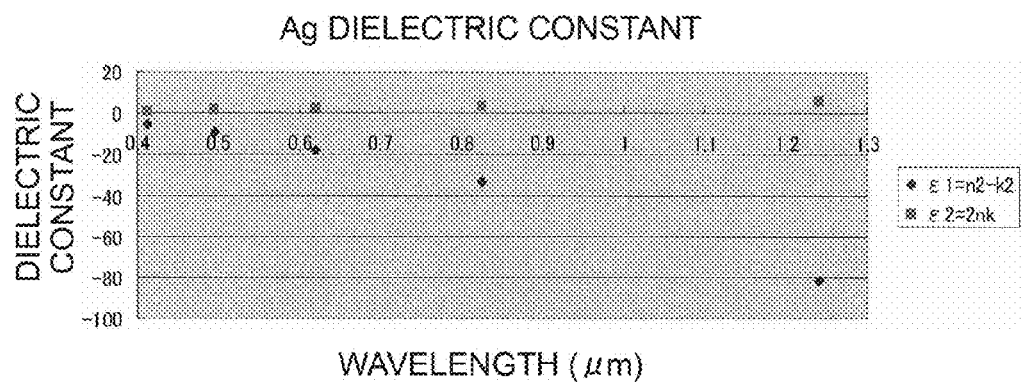
FIG. 7 is a graph showing the relationship between a dielectric constant of Ag and a wavelength.

FIG. 7 is a graph showing the relationship between the dielectric constant of Ag and wavelength. For example, although the dielectric constant of Ag is as shown in FIG. 7, and the localized surface plasmon is excited at a wavelength of about 400 nm, if a plurality of Ag particles are close to each other in a nano order or if the Ag particles and the metal layer 10 (Au film or the like) are arranged to be separated by the light transmitting layer 30 ($SiO_2$ or the like), the peak wavelength of the localized surface plasmon is red-shifted (shifted to a long wavelength side) by the effect of the gap. Although the shift amount depends on dimension, such as Ag diameter, Ag thickness, Ag particle interval, or light transmitting layer thickness, for example, a wavelength characteristic that the localized surface plasmon has a peak at 500 nm to 900 nm is exhibited.

Unlike the propagated surface plasmon, the localized surface plasmon is plasmon which has no speed and does not move, and if the localized surface plasmon is plotted in the graph of the dispersion relation, the slope is zero, that is, ω/k=0.

Figure 8:
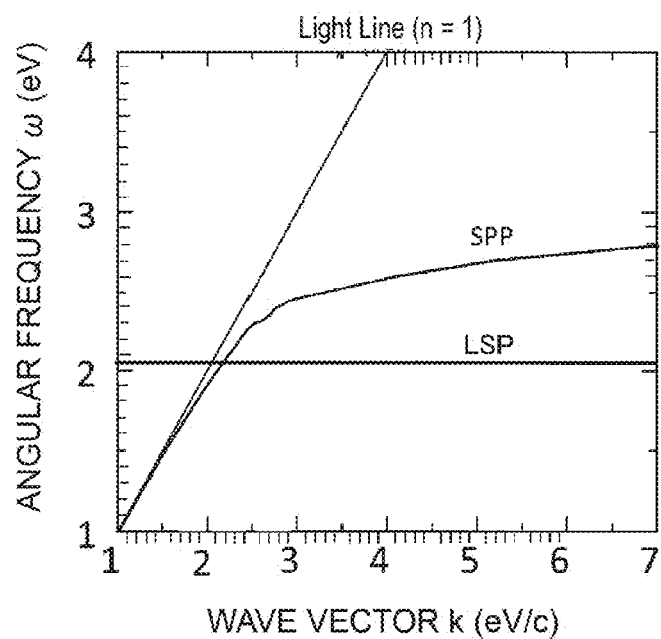
FIG. 8 is a graph showing a dispersion relation of a dispersion curve of a metal, a localized surface plasmon, and incident light.

FIG. 8 is a graph showing a dispersion relation of a dispersion curve of a metal, a localized surface plasmon, and incident light. The optical element 100 of this embodiment electromagnetically couples the propagated surface plasmon and the localized surface plasmon, thereby obtaining an extremely large enhancement degree of an electric field. That is, the optical element 100 of this embodiment has a feature that the intersection point of the line of diffracted light and the dispersion curve of SPP of the metal in the graph of the dispersion relation is not set to an arbitrary point, and both intersect near a point at which the greatest or maximum enhancement degree is given in the localized surface plasmon generated in the metal particles 20 (metal particle columns 21) (see FIG. 8).

In other words, in the optical element 100 of this embodiment, it is designed such that, in the graph of the dispersion relation, the line of diffracted light passes near the intersection point of the dispersion curve of SPP of the metal and the angular frequency (a line parallel to the horizontal axis marked with LSP on the graph of the dispersion relation of FIG. 8) of incident light giving the greatest or maximum enhancement degree in the localized surface plasmon generated in the metal particles 20 (metal particle columns 21).

Here, if converted to wavelength, near the intersection point refers to within the range of a wavelength having a length of about ±10% of the wavelength of incident light, or within the range of a wavelength having a length of about ±P1 (the interval of the metal particles 20 in the metal particle columns 21) of the wavelength of incident light.

In Expressions (3), (4), and (2), although the condition that the propagated surface plasmon is excited when the angular frequency of incident light incident on the metal layer 10 is ω has been described, in order to cause interaction (hybrid) of the localized surface plasmon and the propagated surface plasmon, in the optical element 100 of this embodiment, ω in Expressions (3), (4), and (2) becomes the angular frequency of incident light giving the greatest or maximum enhancement degree in the localized surface plasmon generated in the metal particles 20 (metal particle columns 21) or an angular frequency near the angular frequency of incident light.

Accordingly, when the angular frequency of the localized surface plasmon which is excited in the metal particle columns 21 is ω, if Expression (2) is satisfied, it is possible to cause a hybrid of the localized surface plasmon and the propagated surface plasmon.

Accordingly, when the angular frequency of the localized surface plasmon generated in the metal particle column 21 having the metal particles 20 arranged at the interval P1 is ω, if the line of diffracted light (order m) which is incident on the virtual diffraction gratings having the interval Q at the irradiation angle θ and is diffracted passes near the position of ω of the dispersion curve of SPP of the metal in the graph of the dispersion relation (if Expression (2) is satisfied), it is possible to cause a hybrid of the localized surface plasmon and the propagated surface plasmon, and to obtain an extremely large enhancement degree. In other words, in the graph of the dispersion relation shown in FIG. 8, the slope and/or slice of the light line changes to change the light line so as to pass near the intersection point of SPP and LSP, whereby it is possible to cause a hybrid of the localized surface plasmon and the propagated surface plasmon, and to obtain an extremely large enhancement degree.

1.3.2. Interval P2

The interval P2 between the metal particle columns 21 is set as follows. When vertical incidence (incidence angle θ=0) is made and first-order diffracted light (m=0) is used, if the interval P2 is set as the interval Q, Expression (2) can be satisfied. However, the interval Q at which Expression (2) can be satisfied by the incidence angle θ and the order m of diffracted light to be selected has a width. Although it is preferable that the incidence angle θ in this case is the inclination angle from the thickness direction to the second direction, the incidence angle may be the inclination angle in a direction including the component of the first direction.

Accordingly, the range of the column interval P2 which can cause a hybrid of the localized surface plasmon and the propagated surface plasmon is given by Expression (6) taking into consideration the presence near the intersection point (the width of ±P1).

$$Q-P1 \le P2 \le Q+P1 \qquad (6)$$

Although the interval P2 is the interval between the metal particle columns 21 in the second direction, in regard to the interval between two metal particles 20 belonging to adjacent metal particle columns 21, the line which connects these metal particles 20 can be inclined with respect to the second direction by a method of selecting two metal particles 20. That is, two metal particles 20 belonging to adjacent metal particle columns 21 can be selected so as to have an interval longer than the interval P2. In FIG. 2, an auxiliary line for describing this is drawn, and two metal particles 20 which are separated at a distance longer than the interval P2 in a direction inclined with respect to the second direction can be selected from adjacent metal particle columns 21. As described above, since adjacent metal particle columns 21 are the same metal particle column 21, the arrangement of the metal particles 20 when viewed from the thickness direction may be regarded as a two-dimensional lattice with the positions of the metal particles 20 as lattice points. In the two-dimensional lattice, there is an interval (diffraction grating) longer than the interval P2.

Accordingly, in the matrix of the metal particles 20 arranged at the interval P1 and the interval P2, diffracted light by diffraction gratings having an interval greater than the interval P2 can be expected. For this reason, an inequality expression on the left side of Expression (6) can be defined as P1<P2. In other words, in Expression (6), even if the column interval P2 is smaller than Q−P1, since there may be diffraction gratings having the interval Q at which Expression (2) can be satisfied, it is possible to cause a hybrid of the localized surface plasmon and the propagated surface plasmon. Therefore, the interval P2 may be a value smaller than Q−P1, and it should suffice that the relationship of P1<P2 is satisfied.

From above, if the interval P2 between the metal particle columns 21 in the optical element 100 of this embodiment satisfies the relationship of Expression (1), it is possible to cause a hybrid of the localized surface plasmon and the propagated surface plasmon.

$$P1 < P2 \le Q+P1 \qquad (1)$$

1.4. Light Transmitting Layer

The optical element 100 of this embodiment has the light transmitting layer 30 which separates the metal layer 10 from the metal particles 20. In FIGS. 1, 3, and 4, the light transmitting layer 30 is drawn. The light transmitting layer 30 may have a shape of a film, a layer, or a membrane. The light transmitting layer 30 is provided on the metal layer 10. Accordingly, it is possible to separate the metal layer 10 from the metal particles 20.

The light transmitting layer 30 can be formed by, for example, a method, such as vapor deposition, sputtering, CVD, or various kinds of coating. The light transmitting layer 30 may be provided on the entire surface of the metal layer 10 or may be provided on a part of the surface of the metal layer 10. The thickness of the light transmitting layer 30 is not particularly limited insofar as the propagated surface plasmon of the metal layer 10 and the localized surface plasmon of the metal particles 20 can interact with each other, and even in a thick gap structure using a higher-order interference effect, the effects can be obtained. The thickness of the light transmitting layer 30 can be, for example, equal to or greater than 1 nm and equal to or smaller than 1 μm, preferably, equal to or greater than 5 nm and equal to or smaller than 500 nm, more preferably, equal to or greater than 10 nm and equal to or smaller than 100 nm, still more preferably, equal to or greater than 15 nm and equal to or smaller than 80 nm, and particularly preferably, equal to or greater than 20 nm and equal to or smaller than 60 nm.

The light transmitting layer 30 may have a positive dielectric constant, and may be formed of, for example, $SiO_2$, $Al_2O_3$, $TiO_2$, a polymer, ITO (Indium Tin Oxide), or the like. The light transmitting layer 30 may be made of a dielectric. The light transmitting layer 30 may have a plurality of layers of different materials.

If the light transmitting layer 30 is provided, since there is a case where the excitation peak frequency of the localized surface plasmon generated in the metal particles 20 is shifted, it is desirable to take this into consideration in obtaining the peak excitation wavelength of the localized surface plasmon upon setting of the interval P2.

1.5. Other Configurations and Modification

1.5.1. Overlayer

The optical element 100 of this embodiment may have an overlayer as desired. Though not shown, the overlayer may be formed so as to cover the metal particles 20. The overlayer may also be formed so as to expose the metal particles 20 and to cover other configurations.

For example, the overlayer has a function of mechanically and chemically protecting the metal particles 20 or other configurations from the environment. The overlayer may be formed by a method, for example, vapor deposition, sputtering, CVD, various kinds of coating, or the like. The thickness of the overlayer is not particularly limited. The material of the overlayer is not particularly limited, and the overlayer may be formed of, for example, a metal, such as ITO, Cu, or Al, a polymer, or the like, as well as an insulator, such as $SiO_2$, $Al_2O_3$, or $TiO_2$. It is desirable that the thickness of the overlayer is thin so as to be equal to or smaller than several nm.

If the overlayer is provided, similarly to the light transmitting layer 30, since there is a case where the excitation peak frequency of the localized surface plasmon generated in the metal particles 20 is shifted, it is desirable to take this into consideration in obtaining the peak excitation wavelength of the localized surface plasmon upon setting of the column interval P2.

1.5.2. Modification

Figure 9:
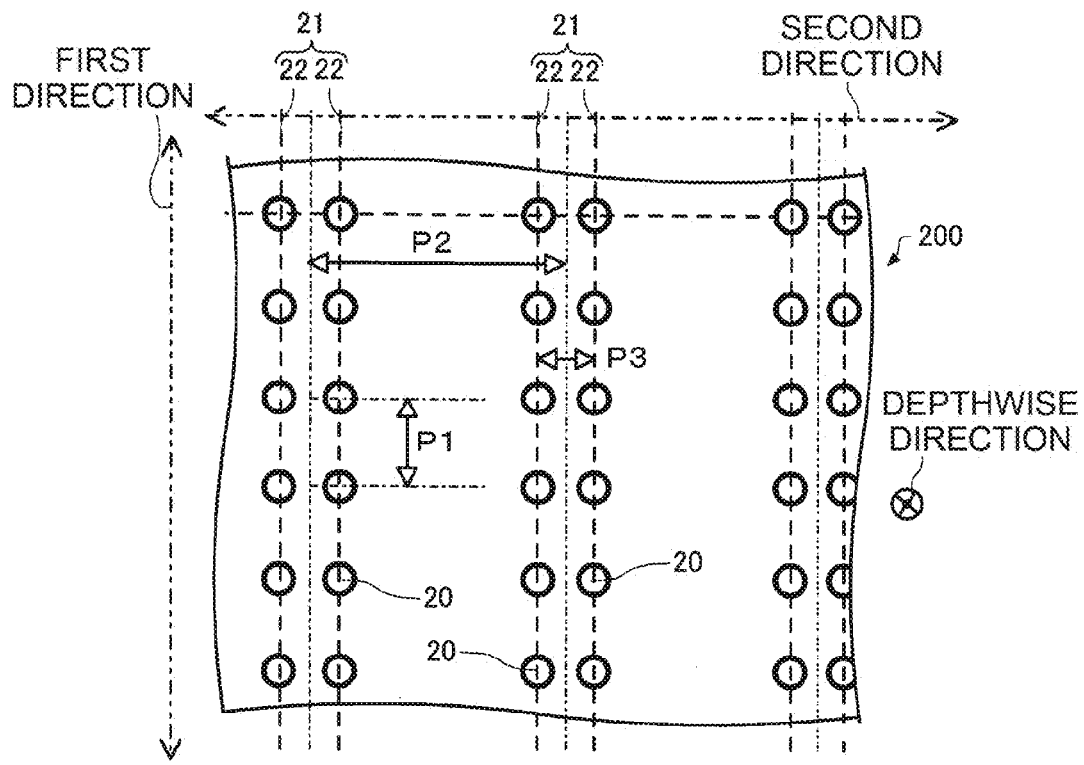
FIG. 9 is a schematic view when an optical element of a modification example of the embodiment is viewed from a thickness direction of a light transmitting layer.

FIG. 9 is a schematic view when an optical element 200 according to a modification example is viewed from the thickness direction. The metal particle columns 21 may have a plurality of columns 22. The columns 22 have a plurality of metal particles 20 arranged at the interval P1 in the first direction, and are the same as the metal particle columns 21. Accordingly, all of a plurality of columns 22 are parallel to the first direction. The angle between a line in the first direction which connects two adjacent metal particles 20 of the same column 22 and a line which connects the closest metal particles 20 among the metal particles 20 belonging to adjacent columns 22 is not particularly limited, and may or may not be a right angle. In the example shown in the drawing, a case where the angle between both lines is a right angle is described.

Here, the interval between adjacent columns 22 is defined as an interval P3 (see FIG. 9). The interval P3 indicates the inter-center distance (pitch) between two columns 22 in the second direction. The interval P3 may have the relationship of P3≤P1 with respect to the interval P1 between the metal particles 20 in the first direction.

If the metal particle columns 21 have columns 22 of a (where a is an integer equal to or greater than 2), the metal particle columns 21 have a width of (a−1)·P3 in the second direction, and have a maximum of (a−1)·P1. Accordingly, in this case, there is a limit to the minimum value of the interval P2, and the minimum value of the interval P2 becomes a·P3<P2. In the example shown in the drawing, the metal particle columns 21 have two columns 22, the metal particle columns 21 have a maximum of the width of P1 in the second direction, and the minimum value of the interval P2 becomes 2·P3<P2.

Even in the optical element 200 according to the modification example, similarly to the optical element 100, it is possible to enhance light with a very high enhancement degree on the basis of plasmon to be excited by light irradiation.

1.6. Method of Designing Optical Element

The optical element 100 of this embodiment has the above-described structure, and hereinafter, a method of designing an optical element will be specifically described.

First, an optical element is designed including selecting the interval P2 such that the line of diffracted light of the localized surface plasmon generated in the metal particle column 21 intersects near the intersection point of the dispersion curve of the metal constituting the metal layer 10 and the angular frequency [ω (eV)] of light giving the peak of the localized surface plasmon excited in the metal particles 20 (metal particle columns 21) arranged at the interval P1 in the graph (the vertical axis is an angular frequency [ω (eV)] and the horizontal axis is a wave vector [k (eV/c)]) of the dispersion relation (see FIG. 8).

A method of designing the optical element of this embodiment includes the following process.

The excitation wavelength dependence of the localized surface plasmon in the metal particles 20 (metal particle columns 21) is examined, and the wavelength at which the greatest or maximum localized surface plasmon is generated in the metal particles 20 (in this specification, this is referred to as a peak excitation wavelength) is recognized. As described above, although the localized surface plasmon changes depending on the material, shape, and the arrangement of the metal particles 20, the presence/absence of other configurations, or the like, the peak excitation wavelength can be obtained by measurement or computation.

The dispersion curve of the metal constituting the metal layer 10 is recognized. This curve may be obtained from the literature or the like depending on the material of the metal layer 10, or may be obtained by computation. From the left side of Expression (2), it is understood that the dispersion relation changes with the ambient refractive index ∈ of the metal layer 10.

The obtained peak excitation wavelength and the dispersion curve are plotted in the graph (the vertical axis is an angular frequency [ω (eV)] and the horizontal axis is a wave vector [k (eV/c)]) of the dispersion relation. At this time, the peak excitation wavelength of the localized surface plasmon becomes a line parallel to the horizontal axis on the graph. Though described above, since the localized surface plasmon is plasmon which has no speed and does not move, if the localized surface plasmon is plotted in the graph of the dispersion relation, the slope (ω/k) becomes zero.

The incidence angle θ of incident light and the order m of diffracted light to be used are determined, the value of Q is obtained from Expression (2), and the interval P2 is selected so as to satisfy the condition of Expression (1). Then, the metal particle columns 21 are arranged.

If at least the above-described process is performed to set the interval P1 and the interval P2, since LSP and PSP are in an interaction (hybrid) state, it is possible to design an optical element having a very large enhancement degree.

1.7. Enhancement Degree

With the mesh position of FDTD computation, the magnitude relationship between an electric field Ex in an X direction (first direction) and an electric field Ez in a Z direction (thickness direction), that is, a vector changes. If linearly polarized light in the X direction is used as excited light, the electric field Ey in the Y direction (second direction) is nearly negligible. For this reason, the enhancement degree can be recognized using the square root of the sum of the squares of Ex and Ez, that is, $SQRT(Ex^2+Ez^2)$. With this, it is possible to perform comparison of the scalars of local fields.

The SERS (Surface Enhancement Raman Scattering) effect is expressed by Expression (a) using hot spot density (HSD) as SERS EF (Enhancement Factor) when an electric field enhancement degree at a wavelength of excited light is Ei, and an electric field enhancement degree at a wavelength after Raman scattering is Es.

$$\text{SERS EF} = Ei^2 \cdot Es^2 \cdot \text{HSD} \qquad (a)$$

Here, for example, since a scattering wavelength is 638 nm, and the difference between the scattering wavelength and the excitation wavelength is equal to or smaller than 40 nm, Stokes scattering equal to or smaller than 1000 $cm^{-1}$ at the excitation wavelength of 600 nm can be approximated as follows (Emax is the greatest enhancement degree).

$$Ei^2 \cdot Es^2 \approx Emax^4$$

Accordingly, Expression (a) can be substituted with Expression (b).

$$SERS\ EF = E\max^4 \cdot HSD \quad (b)$$

That is, it can be considered that SERS (Surface Enhancement Raman Scattering) is obtained by multiplication of hot spot density and the fourth power of the electric field enhancement degree by plasmon.

In an experimental example described below, in regard to Expression (b), HSD is normalized, and Expression (c) is defined and shown.

$$SERS\ EF = (Ex^4 + Ez^4)/\text{Unit Area} \quad (c)$$

If the enhancement degree of the optical element 100 is considered, it is desirable to take into consideration so-called hot spot density (HSD). That is, the enhancement degree of light by the optical element 100 depends on the number of metal particles 20 per unit area of the optical element 100.

In the optical element 100 of this embodiment, the interval P1 and the interval P2 are set such that the relationship of Expressions (1) and (2) is satisfied. However, if HSD is taken into consideration, the SERS enhancement degree of the optical element 100 is proportional to $(Ex^4+Ez^4)/(P1 \cdot P2)$.

1.8. Incident Light

The wavelength of incident light incident on the optical element 100 is not limited insofar as the localized surface plasmon is generated and the relationship of Expression (2) is satisfied, and electromagnetic waves including ultraviolet light, visible light, and infrared light may be used. In this embodiment, incident light is linearly polarized light. In this embodiment, incident light is linearly polarized light whose electric field is in the same direction as the first direction (the extension direction of the metal particle columns 21) of the optical element 100 (see FIGS. 1 to 5). With this, it is possible to obtain a very large enhancement degree of light by the optical element 100.

The optical element 100 of this embodiment has the following features.

The optical element 100 of this embodiment can enhance light with a very high enhancement degree and high HSD on the basis of plasmon to be excited by light irradiation. Since the optical element 100 of this embodiment has a high enhancement degree, for example, the optical element 100 of this embodiment can be used in a sensor which quickly and simply detects bio-related materials, such as bacteria, viruses, protein, nucleic acids, or various antigens/antibodies, or various compounds including inorganic molecules, organic molecules, and polymers with high sensitivity and high precision in the field of medicine and health, environment, food, public safety, and the like. For example, the enhancement degree when an antibody is coupled to the metal particles 20 of the optical element 100 of this embodiment may be obtained, and the presence/absence or the amount of an antigen may be examined on the basis of change in enhancement degree when the antigen is coupled to the antibody. The enhancement degree of light of the optical element 100 of this embodiment can be used to enhance Raman scattering light of trace substances.

2. Analysis Device

Figure 10:
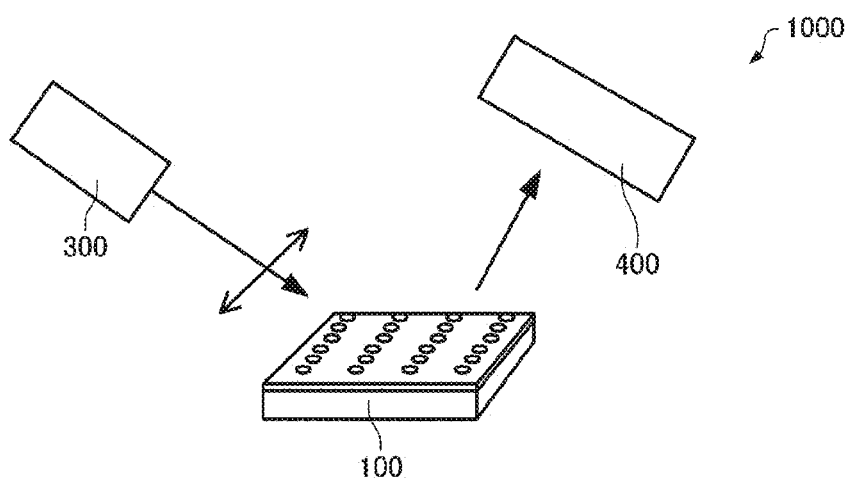
FIG. 10 is a schematic view of an analysis device of an embodiment.

FIG. 10 is a diagram schematically showing a main part of an analysis device 1000 of this embodiment.

The analysis device 1000 of this embodiment includes the above-described optical element 100, a light source 300 which irradiates incident light of linearly polarized light in the same direction as the first direction onto the optical element 100, and a detector 400 which detects light emitted from the optical element 100. The analysis device 1000 of this embodiment may include other appropriate configurations (not shown).

2.1. Optical Element

The analysis device 1000 of this embodiment includes the optical element 100. Since the optical element 100 is the same as the above-described optical element 100, detailed description will not be repeated.

The optical element 100 serves an operation to enhance light and/or an operation as a sensor in the analysis device 1000. The optical element 100 may be used in contact with a sample to be analyzed by the analysis device 1000. The arrangement of the optical element 100 in the analysis device 1000 is not particularly limited, and the optical element 100 may be installed on a stage or the like on which an installation angle or the like is adjustable.

2.2. Light Source

The analysis device 1000 of this embodiment includes the light source 300. The light source 300 irradiates incident light onto the optical element 100. The light source 300 is arranged so as to irradiate linearly polarized light (linearly polarized light in the same direction as the first direction) in the first direction (the direction in which the metal particles 20 are arranged and the direction in which the metal particle columns 21 extend) of the optical element 100 (see FIG. 10). The incidence angle θ of incident light irradiated from the light source 300 may appropriately change in accordance with the excitation conditions of the surface plasmon of the optical element 100. The light source 300 may be installed in a goniometer or the like.

Light irradiated from the light source 300 is not particularly limited insofar as the surface plasmon of the optical element 100 can be excited, and electromagnetic waves including ultraviolet light, visible light, and infrared light may be used. Light irradiated from the light source 300 may or may not be coherent light. Specifically, as the light source 300, a light source in which a wavelength selection element, a filter, a polarizer, and the like are appropriately provided in a semiconductor laser, a gas laser, a halogen lamp, a high-pressure mercury vapor lamp, a xenon lamp, or the like may be used.

Light from the light source 300 becomes incident light, and enhanced light is emitted from the optical element 100. Accordingly, it is possible to perform amplification of Raman scattering light of the sample or detection of a substance interacting with the optical element 100.

2.3. Detector

The analysis device 1000 of this embodiment includes the detector 400. The detector 400 detects light emitted from the optical element 100. As the detector 400, for example, a CCD (Charge Coupled Device), a photomultiplier tube, a photodiode, an imaging plate, or the like may be used.

It should suffice that the detector 400 is provided at a position at which light emitted from the optical element 100 can be detected, and the positional relationship with the light source 300 is not particularly limited. The detector 400 may be installed in a goniometer or the like.

2.4. Analysis Method

An analysis method of this embodiment which irradiates incident light onto the above-described optical element 100, detects light emitted from the optical element 100 with irradiation of incident light, and analyzes an object stuck to the surface of the optical element 100 is performed by irradiating incident light of linearly polarized light onto the optical element 100 in the same direction as the first direction (the direction in which the metal particles 20 are arranged and the direction in which the metal particle columns 21 extend).

3. Electronic Apparatus

An electronic apparatus 2000 of this embodiment includes the above-described analysis device 1000, a calculation unit 2010 which calculates health and medical information on the basis of detection information from the detector 400, a storage unit 2020 which stores the health and medical information, and a display unit 2030 which displays the health and medical information.

Figure 11:
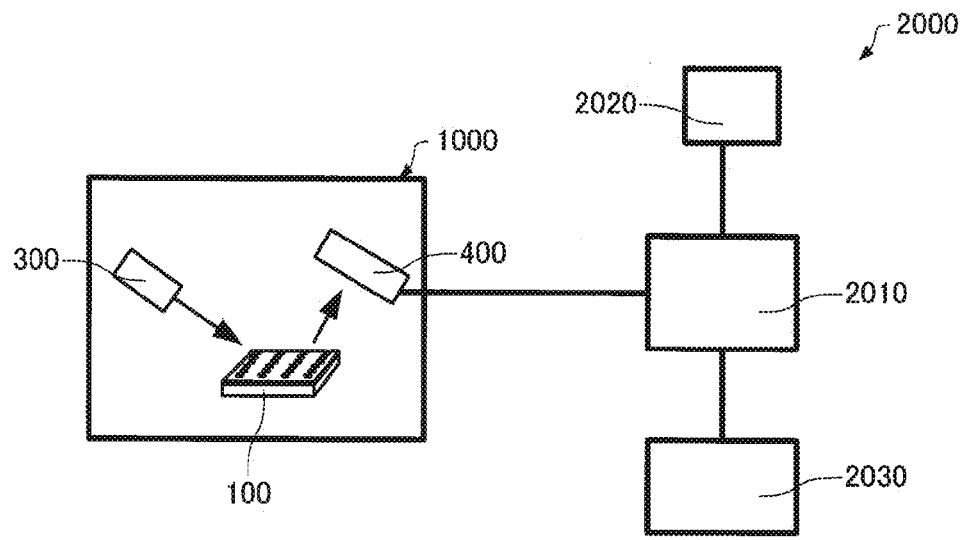
FIG. 11 is a schematic view of an electronic apparatus of an embodiment.

FIG. 11 is a schematic view showing the configuration of the electronic apparatus 2000 of this embodiment. The analysis device 1000 is the analysis device 1000 described in "2. Analysis Device", and detailed description will not be repeated.

The calculation unit 2010 is, for example, a personal computer or a personal digital assistance (PDA), receives the detection information (signal or the like) transmitted from the detector 400, and performs calculation based on the detection information. The calculation unit 2010 may control the analysis device 1000. For example, the calculation unit 2010 may control the output, position, or the like of the light source 300 of the analysis device 1000 or may control the position or the like of the detector 400. The calculation unit 2010 can calculate the health and medical information on the basis of the detection information from the detector 400. The health and medical information calculated by the calculation unit 2010 is stored in the storage unit 2020.

The storage unit 2020 is, for example, a semiconductor memory, a hard disk drive, or the like, and may be constituted integrally with the calculation unit 2010. The health and medical information stored in the storage unit 2020 is transmitted to the display unit 2030.

The display unit 2030 is constituted by, for example, a display board (liquid crystal monitor or the like), a printer, an illuminant, a speaker, or the like. The display unit 2030 performs display or gives an alarm on the basis of the health and medical information or the like calculated by the calculation unit 2010 such that the user can recognize the content.

The health and medical information may include information relating to the presence/absence or the amount of at least one bio-related material selected from a group consisting of bacteria, viruses, protein, nucleic acids, and antigens/antibodies or at least one compound selected from inorganic molecules and organic molecules.

4. Experimental Examples

Hereinafter, although the invention will be further described in connection with experimental examples, the invention is not limited to the following examples. The following examples are a simulation by a computer.

4.1. Computation Model

Figure 12:
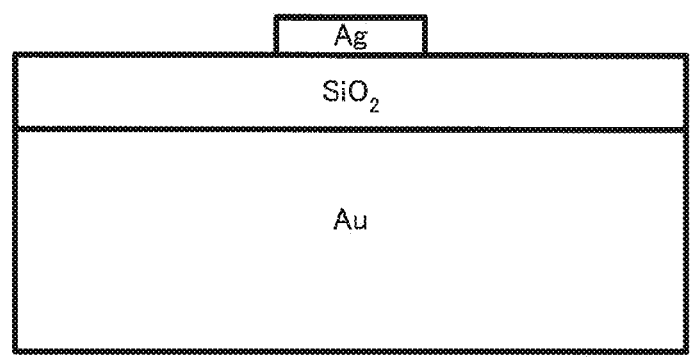
FIG. 12 is a schematic view showing an example of a model according to an experimental example.

FIG. 12 is a schematic view showing the basic structure of a model for use in a simulation.

In all models used for computation of an experimental example, a dielectric layer ($SiO_2$) film was formed on Au (metal layer) which was thick enough to prevent transmission of light. The thickness of the dielectric layer was fixed to 20 nm, 50 nm, or 60 nm. Metal particles arranged on the dielectric layer were Ag, and were a column with the thickness direction of the dielectric layer ($SiO_2$) as a center axis, the size (the diameter of the bottom surface) of the column was 30 nm, 32 nm, or 72 nm, and the height of the column was 4 nm to 20 nm.

FDTD soft Fullwave manufactured by CYBERNET SYSTEMS CO., LTD. was used for computation. The condition of a used mesh was a 1 nm minimum mesh, and the computation time cT was 10 μm.

The ambient refractive index n was 1, and incident light was linearly polarized light in the same direction as the first direction (X) with vertical incidence from the thickness direction (Z) of the metal layer or the light transmitting layer.

In a model having Ag particles arranged in a line at an interval of 60 nm in the second direction (X), a near field characteristic was computed on the top surface of the $SiO_2$ film below the Ag particles, and it was understood that an electric field vector was greatly changed with the arrangement of YeeCell. Accordingly, since it is found that, if an electric field is described by scalar, the effect of the position of YeeCell decreases, and a value at a substantially maximum enhancement position (hot spot) substantially became equal in the X direction and the Z direction, in this experimental example, it is assumed that the enhancement degree is expressed by $SQRT(Ex^2+Ez^2)$. Here, Ex represents electric field intensity in a polarization direction (first direction) of incident light, and Ez represents electric field intensity in the thickness direction. In this case, electric field intensity in the second direction is small and thus not taken into consideration.

4.2. Experimental Example 1

Figure 13:
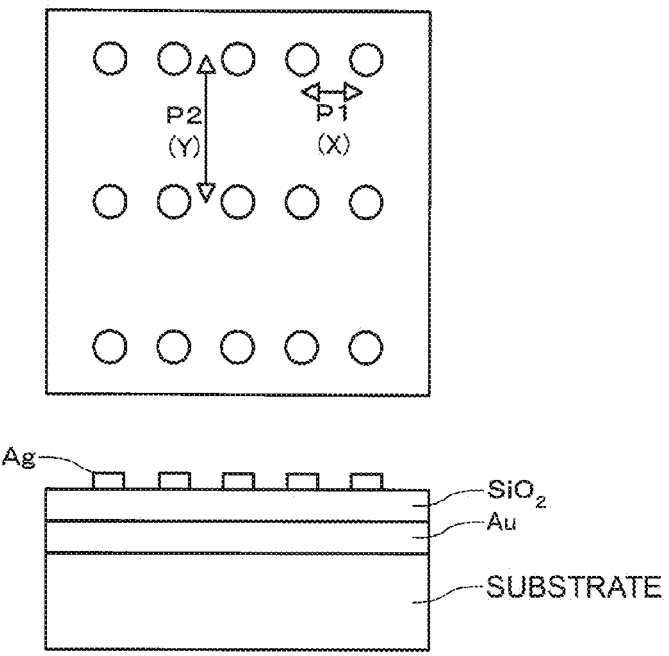
FIG. 13 is a schematic view showing a model according to an experimental example.

FIG. 13 is a diagram schematically showing a model used in Experimental Example 1.

While the thickness of the dielectric layer was 50 nm, the size (the diameter of the bottom surface) of the column of the Ag particles having a columnar shape was 30 nm, the interval P1 of the Ag particles in the first direction was fixed to 60 nm, and the interval P2 of the Ag particle columns in the second direction was changed to 60 nm, 480 nm, 540 nm, 600 nm, 660 nm, and 720 nm, excitation wavelength dependence of a near file was examined. Here, the diameter of the bottom surface of the Ag particles was 30 nm. The result is shown in FIG. 14.

Figure 14:
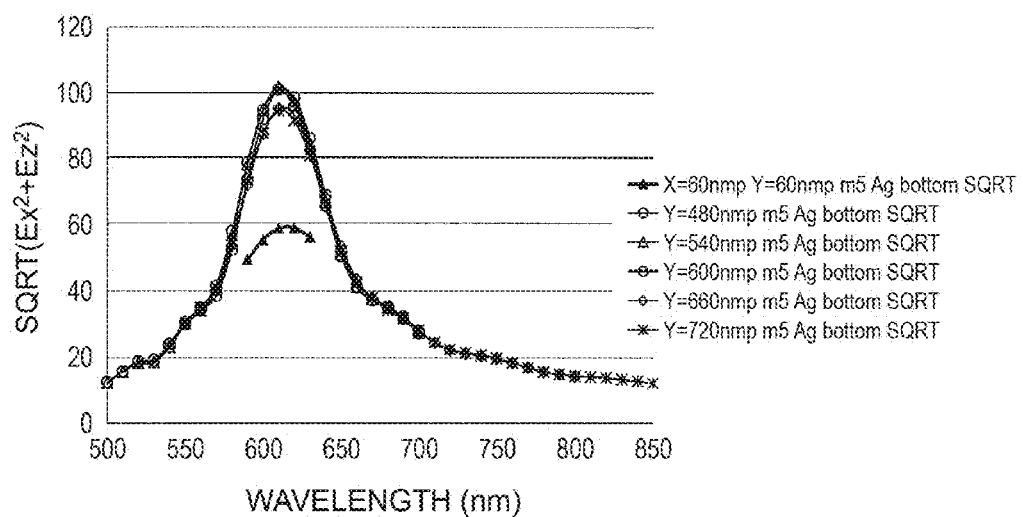
FIG. 14 is a graph showing excitation wavelength dependence of hybrid plasmon according to an experimental example.

Referring to FIG. 14, it was found that, when the interval P2 was 480 nm, 540 nm, 600 nm, 660 nm, and 720 nm, the peak excitation wavelength was 610 nm. In the respective cases, the enhancement degree was 100.9, 101.8, 101.1, 95.1, and 94.4.

In contrast, it was found that, when the interval P2 was 60 nm (that is, P1=P2), the peak excitation wavelength was about 620 nm, and the enhancement degree was about 58.7. The reason for which the peak excitation wavelength becomes 620 nm is considered that, since the distance between the Ag particles in the second direction is 60 nm, red-shift occurs due to the localized surface plasmon.

From this, it was found that, when the interval P2 was 480 nm, 540 nm, 600 nm, 660 nm, and 720 nm, a significantly large enhancement degree is exhibited compared to when the interval P2 is 60 nm. When the interval P2 was 480 nm to 720 nm, in particular, when the interval P2 is 540 nm and 600 nm, the reason that a larger enhancement degree is exhibited can be explained by a graph (FIG. 15) of a dispersion relation.

Figure 15:
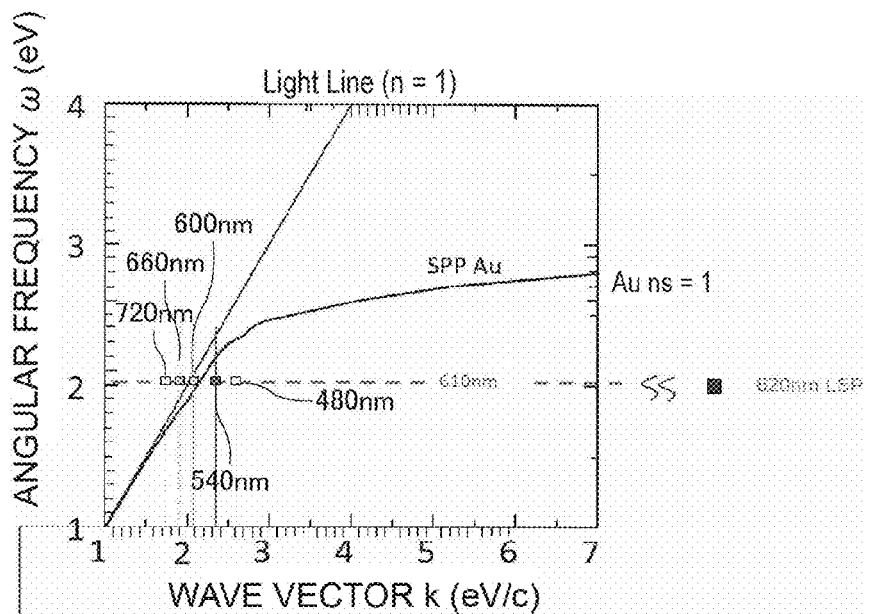
FIG. 15 is a graph of a dispersion relation according to an experimental example.

That is, the reason is considered that, if the interval P2 is 540 nm and 600 nm, this is closer to the intersection point of the peak excitation wavelength (610 nm) of the localized surface plasmon of the Ag particles and SPP of Au in the graph of the dispersion relation of FIG. 15.

With this experimental example, it was found that, even if the interval P2 was changed, the peak excitation wavelength of the localized surface plasmon was not changed, and a hybrid with the propagated surface plasmon of the Au layer was attained and a high enhancement degree was obtained depending on the size of the interval P2.

4.3. Experimental Example 2

A simulation was performed in the same manner as in Experimental Example 1, except that the thickness of the dielectric layer was 60 nm, and the size (the diameter of the bottom surface) of the Ag particles having a columnar shape was 32 nm.

According to this model, the peak excitation wavelength was 633 nm. $SQRT(Ex^2+Ez^2)$ at this time was 67.9. Hereinafter, as shown in Experimental Example 1, since the peak excitation wavelength was not changed by the interval P2, the peak excitation wavelength was fixed to 633 nm, and the interval P2 was a variable.

While the interval P1 of the Ag particles in the first direction was fixed to 60 nm, and the interval P2 of the Ag particle columns in the second direction was changed, change of the enhancement degree with respect to the interval P2 was obtained. The result is shown in FIG. 16.

Figure 16:
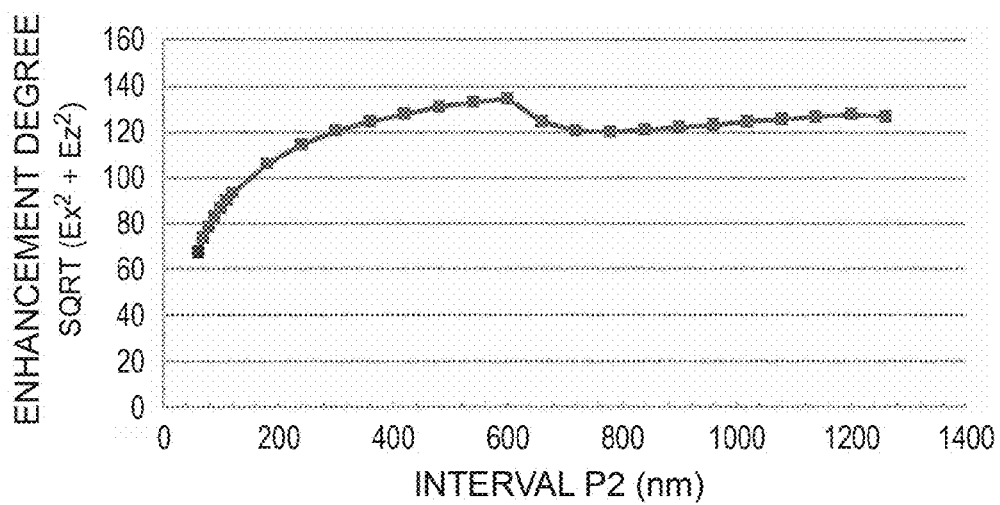
FIG. 16 is a graph showing the relationship between an enhancement degree and an interval according to an experimental example.

Referring to FIG. 16, as the interval P2 became larger from 60 nm, the enhancement degree immediately increased, and the enhancement degree had a maximum value at 600 nm. If the interval P2 became larger, while the enhancement degree slightly decreased, the enhancement degree increased while a high enhancement degree was maintained, and had two peak values when the interval P2 was 1200 nm.

From this, it is understood that the Ag particles and the Au film interact with each other. It was found that, a hybrid with the propagated surface plasmon of the Au layer was attained and a high enhancement degree was obtained depending on the size of the interval P2.

Referring to FIG. 16, for example, even in a region where the interval P2 was small, for example, the interval P2 was 120 nm (93.1), it was understood that a significantly large enhancement degree 1.37 times the enhancement degree (67.9) when the interval P2 was 60 nm was obtained. The reason is considered that two effects of interaction of SPP of Au and LSP and a hot spot density effect (the effect of concentrating an electric field on a small hot spot if hot spot density decreases) are combined.

Another reason is considered that the Ag particles can be selected such that the interval between two Ag particles belonging to adjacent Ag particle columns is longer than the interval P2 by a way to select two Ag particles. Accordingly, it is considered that there is a grating interval (diffraction grating) longer than the interval P2, and diffracted light by diffraction gratings having the interval occurs. Specifically, as shown in FIG. 2, it is considered that the propagated surface plasmon between diffraction gratings of an oblique component exhibits an enhancement effect if the interval of the diffraction gratings satisfies 600 nm, and resonance (hybrid) with the localized surface plasmon of the metal particles occurs.

Figure 17:
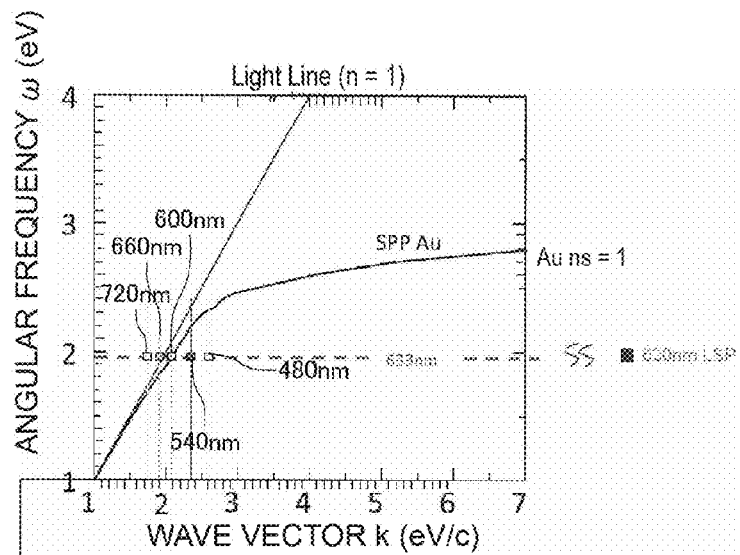
FIG. 17 is a graph of a dispersion relation according to an experimental example.

FIG. 17 shows a graph of a dispersion relation of this experimental example. Referring to FIG. 17, it is confirmed that an intersection point with SPP of Au is near 600 nm, and the enhancement degree has a maximum value at the interval P2=600 nm.

The reason for which the peak of the enhancement degree is present at the interval P2=1200 nm is considered that a multiple of a wavenumber $2\pi/1200$ corresponding to 1200 nm becomes equal to a wavenumber $2\pi/600$ corresponding to 600 nm.

In this experimental example, since the excitation wavelength was 633 nm, the enhancement degree when the interval P2=600 nm was 134.5 and had the highest value close to two times the enhancement degree (67.9) when the interval P2=60 nm.

4.4. Experimental Example 3

If both energy of excitation light and energy of scattering light are utilized, Raman scattering is proportional to the fourth power of an enhanced electric field. That is, it is that Raman scattering is proportional to $E^4$. Accordingly, when the interval P1=60 nm and the interval P2=600 nm of Experimental Example 2, $(134.5/67.9)^4=15.39$. However, in this case, since the number of metal particles per unit area becomes $\frac{1}{10}$ compared to when the interval P1=60 nm and the interval P2=60 nm, the Raman scattering enhancement degree can be estimated as $\frac{15.39}{10}=1.54$. That is, in Experimental Example 2, it is possible to obtain a high Raman scattering enhancement degree of 54%.

Figure 18:
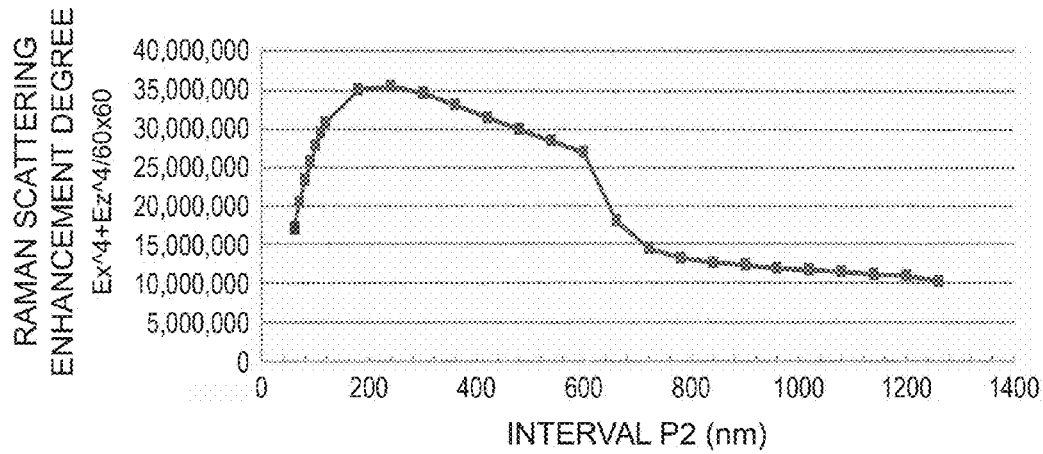
FIG. 18 is a graph showing the relationship between a Raman scattering enhancement degree and an interval according to an experimental example.

Accordingly, the vertical axis of FIG. 16 of Experimental Example 2 was normalized as $(Ex^4+Ez^4)/(P1\cdot P2)$ with hot spot density and plotted in FIG. 18.

From the plot of FIG. 18, the Raman effect is supposed, and by comparison with the sum of the fourth power per unit area, it is found that a high value in a wide range of 60 nm<P2≤660 nm is obtained compared to when the interval P1=60 nm and the interval P2=60 nm.

For example, the value of $(Ex^4+Ez^4)/(P1\cdot P2)$ was 17133729 when P1=60 nm and P2=60 nm, and was 35522039 when P1=60 nm and P2=240 nm.

4.5. Experimental Example 4

A simulation was performed in the same manner as in Experimental Example 1, except that the thickness of the dielectric layer was 20 nm, the size (the diameter of the bottom surface) of the column of the Ag particles having a columnar shape was 72 nm, the height of the column was 20 nm, and the interval P1 was 120 nm.

The peak excitation wavelength of the localized surface plasmon of this model was 633 nm. As shown in FIG. 19, as in Experimental Example 1 and Experimental Example 2, if the interval P2 became larger, the enhancement degree increased. In this experimental example, the enhancement degree had a maximum value at P2=600 nm corresponding to a wavenumber as the intersection point of SPP of Au and the peak excitation wavelength of LSP in the graph of the dispersion relation.

As a result of plotting with the value of $(Ex^4+Ez^4)/(P1\cdot P2)$ (FIG. 20), it was found that a high value in a wide range of 120 nm<P2≤840 nm was obtained compared to a case where the interval P1=120 nm and the interval P2=120 nm.

4.6. Experimental Example 5

When the metal particle columns have a plurality of columns, a simulation was performed using the following model.

Figure 22:
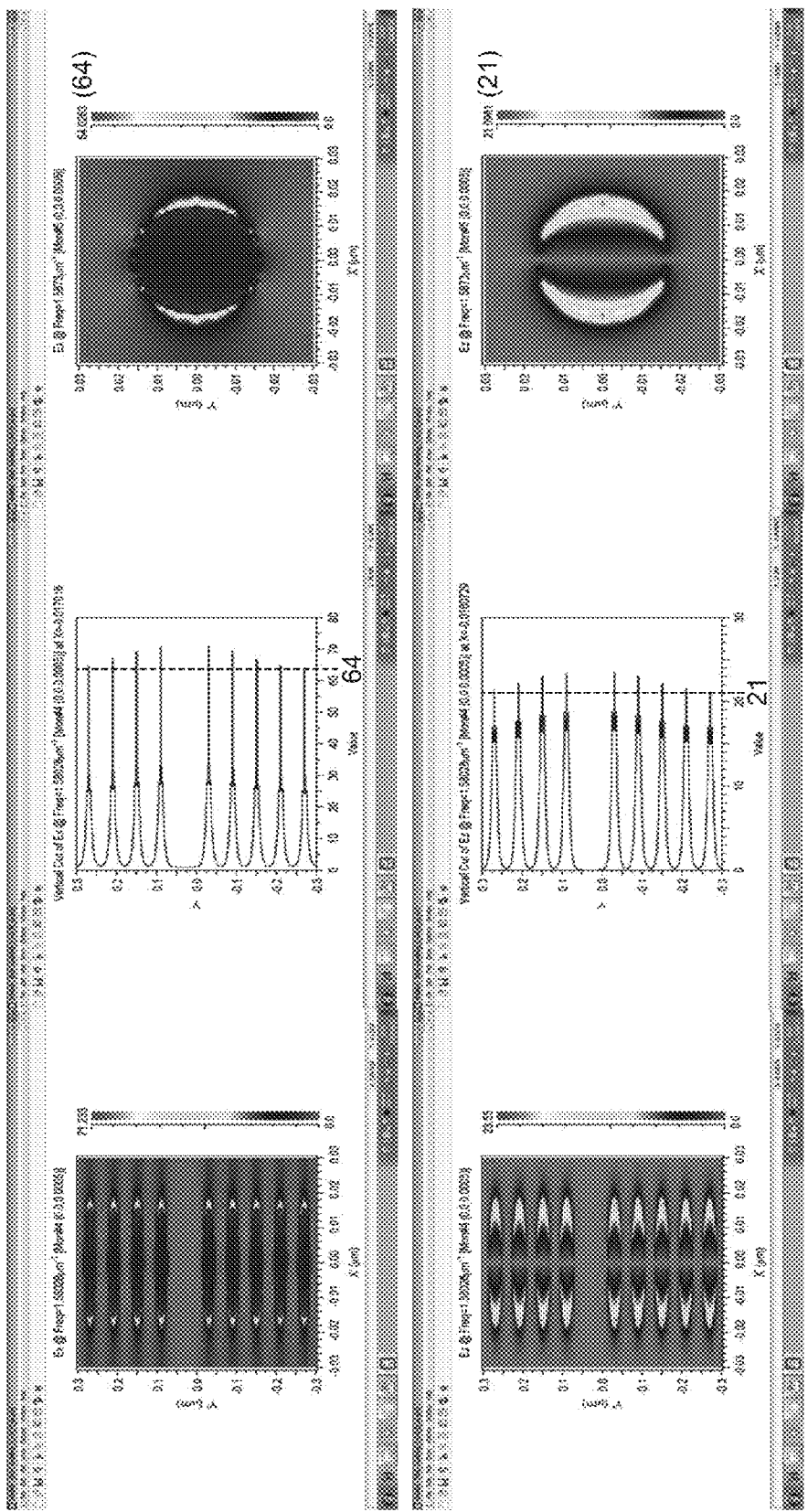
FIG. 22 is a diagram showing a hot spot intensity distribution upon polarization in a first direction.

FIGS. 21A and 21B show a computation model in which the thickness of the dielectric layer is 60 nm, the size (the diameter of the bottom surface) of the column of the Ag particles having a columnar shape is 32 nm, the height of the column is 4 nm, and the interval P1 is 60 nm. FIG. 22 shows a hot spot distribution in a near field when one column of Ag particles is excluded (FIG. 21B). A region used for computation was indicated by a broken line in the drawing. The peak excitation wavelength is 633 nm.

A left view of FIG. 22 shows Ex and Ez of a model in which the interval P2=600 nm. A wavenumber in which a nine-line model occurs becomes a 600 nm pitch. A middle view of FIG. 22 shows a hot spot intensity distribution. A right view of FIG. 22 shows a distribution when the interval P1=60 nm and the interval P2=60 nm. Ex (64) and Ez (21) of the interval P1=the interval P2=60 nm were drawn as an auxiliary line in the middle view of FIG. 22. A model of the interval P2=600 nm exceeded a value when the interval P1=the interval P2=60 nm in all hot spots.

Figure 23:
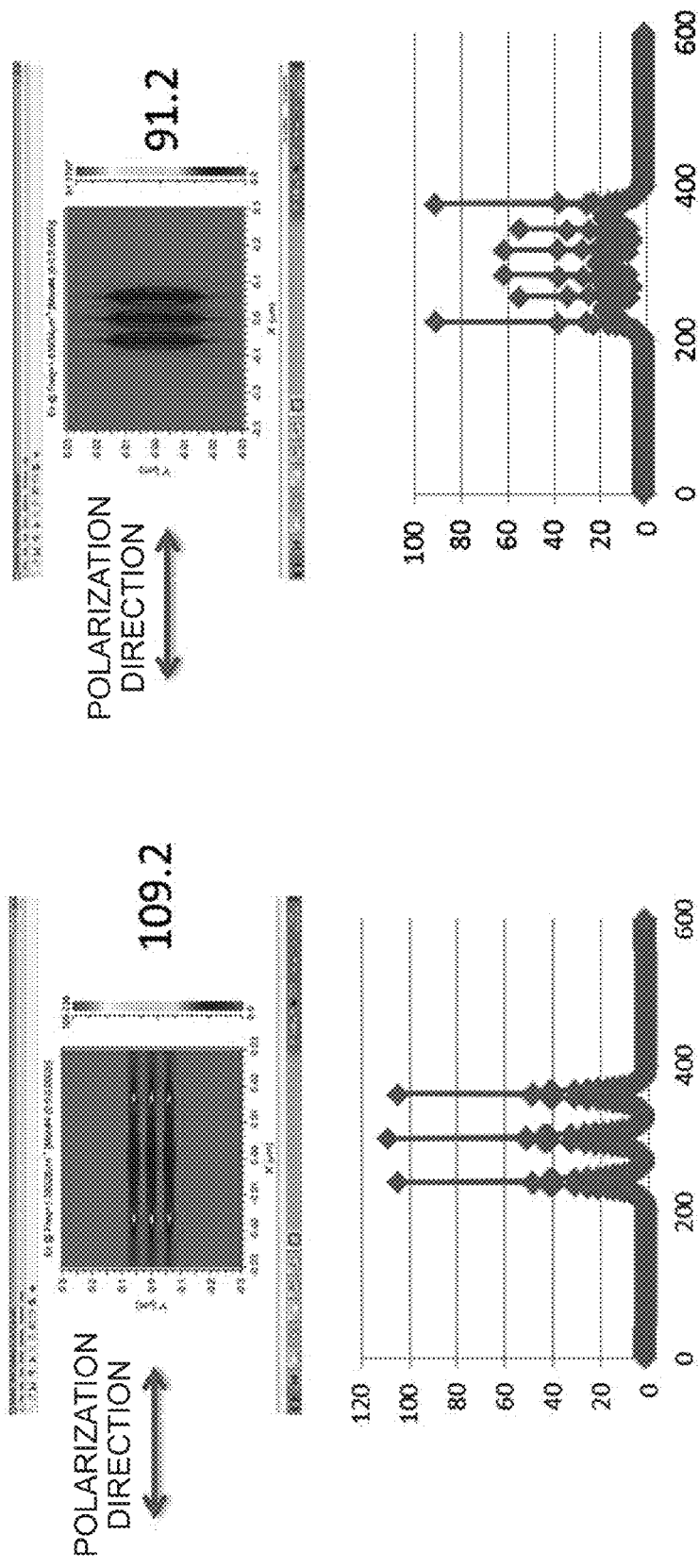
FIG. 23 is a diagram showing a hot spot intensity distribution upon polarization in a first direction.

FIG. 23 shows a comparison result of when the interval P1=60 nm and the interval P2=600 nm and when the interval P1=600 nm and the interval P2=60 nm in a three-line model. The direction of the polarization of excitation light is the same first direction. That is, this is synonymous with a case where the polarization direction of linearly polarized light is the first direction and a case where the polarization direction of the linearly polarized light is the second direction when the interval P1=60 nm and the interval P2=600 nm.

Referring to FIGS. 22 and 23, it was found that, in a case of linearly polarization in the first direction, variation in intensity distribution by the positions of the hot spots was significantly reduced. For this reason, it is understood that this optical element can be suitably used as a concentration sensor.

Figure 24:
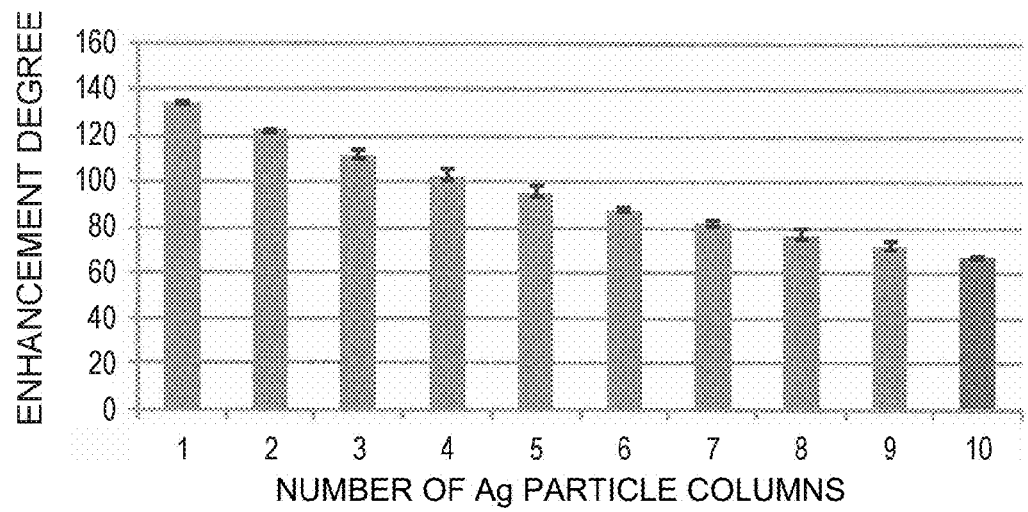
FIG. 24 is a graph showing the relationship between an enhancement degree and the number of Ag particles according to an experimental example.

A simulation was performed with the increased number of excluded Ag particle columns, and it was thus found that hot spot intensity was enhanced compared to a model with no Ag particle columns excluded. The result was collectively shown in FIG. 24. An error bar on a bar graph of FIG. 24 represents a distribution by the positions of the hot spots, and in case of number of Ag particle columns is one and two, it is understood that there is few distribution of intensity.

Figure 25:
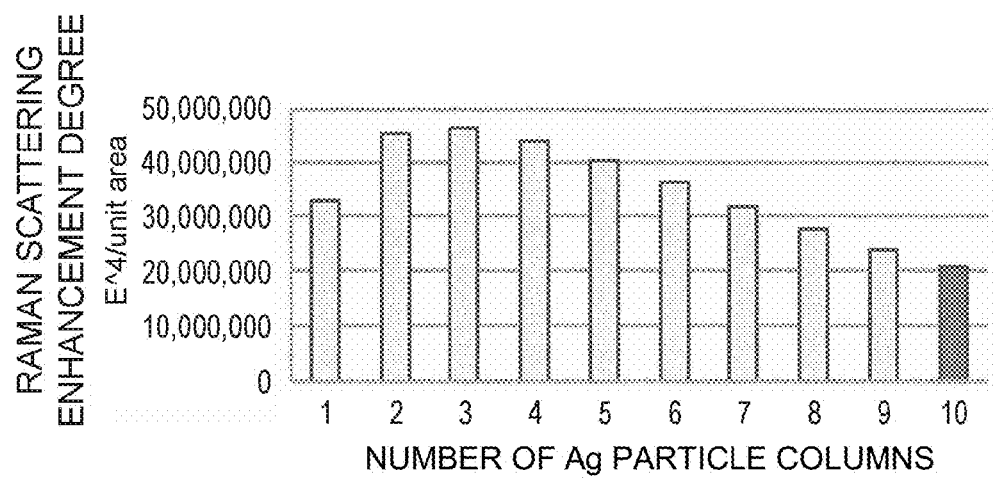
FIG. 25 is a graph showing the relationship between a Raman scattering enhancement degree and the number of Ag particles according to an experimental example.

The Raman enhancement degree per unit area taking into consideration a decrease in hot spot density (HSD) with the exclusion of the Ag particle columns is estimated, and the graphical result of the Raman enhancement degree is shown in FIG. 25. Referring to FIG. 25, the Raman enhancement degree has a maximum value when the number of Ag particle columns is around 2 to 5 and is about two times compared to a model with no Ag particle columns excluded.

4.7. Experimental Example 6

A simulation was performed in the same manner as in experimental Example 5, except that the thickness of the dielectric layer was 20 nm, the size (the diameter of the bottom surface) of the column of the Ag particles having a columnar shape was 72 nm, the height of the column was 20 nm, and the number of Ag particle columns to be arranged was 5. The peak excitation wavelength is 633 nm.

Figure 26:
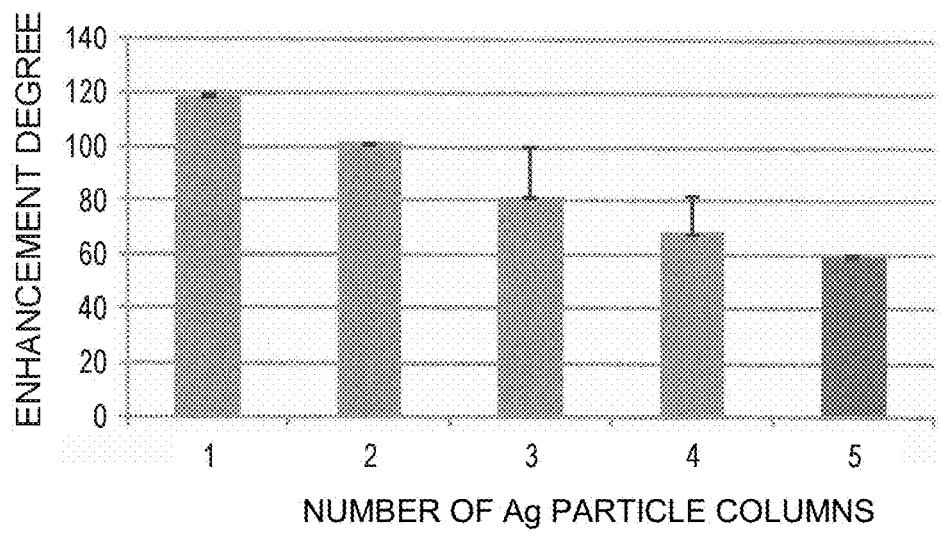
FIG. 26 is a graph showing the relationship between an enhancement degree and the number of Ag particles according to an experimental example.
Figure 27:
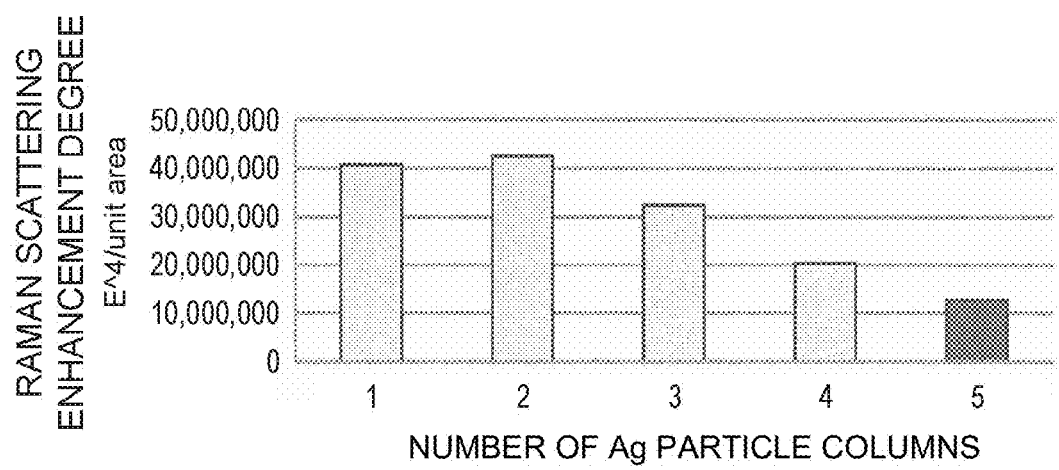
FIG. 27 is a graph showing the relationship between a Raman scattering enhancement degree and the number of Ag particles according to an experimental example.

The result is shown in FIGS. 26 and 27. Referring to FIGS. 26 and 27, a simulation was performed with the increased number of excluded Ag particle columns, and it was thus found that hot spot intensity was enhanced compared to a model with no Ag particle columns excluded.

The Raman enhancement degree per unit area taking into consideration a decrease in hot spot density (HSD) with the exclusion of the Ag particle columns is estimated, and from the graphical result of the Raman enhancement degree (FIG. 27), it is found that, the Raman enhancement degree has a maximum value when the number of Ag particle columns is 2 and is about three times compared to a model with no Ag particles excluded.

The invention is not limited to the foregoing embodiments, and various modifications may be made. For example, the invention includes the substantially same configuration (for example, a configuration having the same functions, method, and result, or a configuration having the same object and effects) as the configurations described in the embodiments. The invention also includes a configuration in which a non-essential portion in the configurations described in the embodiments is substituted. The invention also includes a configuration in which the same functional effects as the configurations described in the embodiments can be obtained or a configuration in which the same object as the configurations described in the embodiments can be attained. The invention also includes a configuration in which a known configuration is added to the configurations described in the embodiments.

The entire disclosure of Japanese Patent Application No. 2013-042666 filed Mar. 5, 2013 is expressly incorporated by reference herein.

What is claimed is:

1. An analysis device comprising:
    an optical element which includes a metal layer, a light transmitting layer provided on the metal layer to transmit light, and a plurality of metal particles arranged on the light transmitting layer at a first interval P1 in a first direction and arranged at a second interval P2 in a second direction intersecting the first direction;
    a light source which irradiates incident light of linearly polarized light in the first direction onto the optical element; and
    a detector which detects light emitted from the optical element,
    wherein P1<P2≤Q+P1;
    wherein Q represents diffraction grating interval given by:

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
    $$(m = \pm 1, \pm 2, \ldots); \text{ and}$$

wherein an angular frequency of a localized surface plasmon excited in a metal particle column is $\omega$, a dielectric constant of a metal constituting the metal layer is $\in(\omega)$, a dielectric constant around the metal layer is $\in$, light speed in a vacuum is c, and an irradiation angle of incident light which is an inclination angle of incident light from a thickness direction of the light transmitting layer is $\theta$.

2. The analysis device according to claim 1, wherein 60 nm≤P2≤1310 nm.

3. The analysis device according to claim 1, wherein 60 nm≤P2≤660 nm.

4. The analysis device according to claim 1, wherein 60 nm≤P1≤120 nm.

5. The analysis device according to claim 1, wherein a size of the metal particles in the first direction is D and 30 nm≤D≤72 nm.

6. The analysis device according to claim 1,
wherein a size of the metal particles in a height direction is T and 4 nm≤T≤20 nm.

7. The analysis device according to claim 1,
wherein the light transmitting layer is a dielectric layer in which a height direction of the metal particles is a thickness direction, and
a thickness of the dielectric layer is G and 20 nm≤G≤60 nm.

8. The analysis device according to claim 1,
wherein the detector detects Raman scattering light enhanced by the optical element.

9. The analysis device according to claim 1,
wherein the light source irradiates incident light having a wavelength greater than a size in a height direction and a size in the first direction of the metal particles onto the optical element.

10. An electronic apparatus comprising:
the analysis device according to claim 1;
a calculation unit which calculates diagnostic information based on detection information from the detector;
a storage unit which stores the diagnostic information; and
a display unit which displays the diagnostic information.

11. The electronic apparatus according to claim 10,
wherein the diagnostic information includes information relating to the presence and/or absence or the amount of at least one bio-related material selected from a group consisting of bacteria, viruses, protein, nucleic acids, and antigens and/or antibodies, or at least one compound selected from inorganic molecules and organic molecules.

12. An analysis method comprising:
providing an optical element;
irradiating the optical element with incident light; and
detecting light emitted from the optical element to analyze an object,
wherein the optical element includes a metal layer, a light transmitting layer provided on the metal layer to transmit light, and a plurality of metal particles arranged at a first interval P1 in a first direction and arranged at a second interval P2 in a second direction intersecting the first direction on the light transmitting layer,
wherein P1<P2≤Q+P1;
wherein incident light of linearly polarized light in the first direction is irradiated onto the optical element; and
wherein Q represents diffraction grating interval given by:

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
$$(m = \pm 1, \pm 2, \ldots); \text{ and}$$

wherein an angular frequency of a localized surface plasmon excited in a metal particle column is $\omega$, a dielectric constant of a metal constituting the metal layer is $\in(\omega)$, a dielectric constant around the metal layer is $\in$, light speed in a vacuum is c, and an irradiation angle of incident light which is an inclination angle of incident light from a thickness direction of the light transmitting layer is $\theta$.

13. A method of manufacturing an optical element comprising:
providing a metal layer;
providing a light transmitting layer on the metal layer to transmit light; and
providing a plurality of metal particles on the light transmitting layer arranged at a first interval P1 in a first direction and arranged at a second interval P2 in a second direction intersecting the first direction,
wherein P1<P2≤Q+P1;
wherein Q represents diffraction grating interval given by:

$$(\omega/c) \cdot \{\in \cdot \in(\omega)/(\in + \in(\omega))\}^{1/2} = \in^{1/2} \cdot (\omega/c) \cdot \sin\theta + 2m\pi/Q$$
$$(m = \pm 1, \pm 2, \ldots); \text{ and}$$

wherein an angular frequency of a localized surface plasmon excited in a metal particle column is $\omega$, a dielectric constant of a metal constituting the metal layer is $\in(\omega)$, a dielectric constant around the metal layer is $\in$, light speed in a vacuum is c, and an irradiation angle of incident light which is an inclination angle of incident light from a thickness direction of the light transmitting layer is $\theta$.

* * * * *